US009566187B2

(12) United States Patent
Edelman et al.

(10) Patent No.: US 9,566,187 B2
(45) Date of Patent: Feb. 14, 2017

(54) COLD THERAPY SYSTEMS AND METHODS

(75) Inventors: Howard Edelman, San Francisco, CA (US); Scott Ganaja, San Luis Obispo, CA (US); Irving M D Hu, San Francisco, CA (US); Mani Razaghi Kashani, Palo Alto, CA (US); Carey Lee, Mountain View, CA (US); Matt Vargas, San Jose, CA (US)

(73) Assignee: Breg, Inc., Carlsbad, CA (US)

( * ) Notice: Subject to any disclaimer, the term of this patent is extended or adjusted under 35 U.S.C. 154(b) by 786 days.

(21) Appl. No.: 13/418,857

(22) Filed: Mar. 13, 2012

(65) Prior Publication Data

US 2013/0245729 A1 Sep. 19, 2013

(51) Int. Cl.
*A61F 7/00* (2006.01)
*A61F 7/10* (2006.01)

(52) U.S. Cl.
CPC .............. *A61F 7/10* (2013.01); *A61F 7/0053* (2013.01); *A61F 7/0085* (2013.01); *A61F 2007/0056* (2013.01); *A61F 2007/0059* (2013.01); *A61F 2007/0069* (2013.01); *A61F 2007/0093* (2013.01)

(58) Field of Classification Search
CPC .............. A61F 2007/0292; A61F 2007/0295; A61F 7/0085
USPC ........................................................ 607/104
See application file for complete search history.

(56) References Cited

U.S. PATENT DOCUMENTS

| | | | |
|---|---|---|---|
| 222,690 A | 12/1879 | Goldschmidt | |
| 1,896,953 A | 5/1931 | Hassell | |
| 2,260,134 A | 10/1939 | Ballman | |
| 2,726,658 A * | 12/1955 | Chessey | A61F 7/10 607/104 |
| 3,007,473 A * | 11/1961 | Jackson | A61F 7/00 165/292 |
| 3,316,732 A | 5/1967 | Burton | |
| 3,587,577 A | 6/1971 | Solyanka | |
| 3,625,279 A | 12/1971 | Mayo | |
| 3,648,765 A | 3/1972 | Starr | |
| 3,744,555 A | 7/1973 | Fletcher et al. | |
| 3,811,431 A | 5/1974 | Apstein | |
| 3,871,381 A * | 3/1975 | Roslonski | 607/104 |

(Continued)

FOREIGN PATENT DOCUMENTS

| | | |
|---|---|---|
| CA | 2601496 | 3/2008 |
| EP | 1990039 | 11/2008 |

(Continued)

OTHER PUBLICATIONS

International Preliminary Report on Patentability issued Mar. 21, 2014 for related International Appln. No. PCT/US2013/029061.

(Continued)

*Primary Examiner* — Ronald Hupczey, Jr.
(74) *Attorney, Agent, or Firm* — Rodney F. Brown

(57) ABSTRACT

A cold therapy system including a cooling bath; a therapy pad in fluid communication with the cooling bath; a pump positioned and arranged to pump water from the cooling bath to the therapy pad and back to the cooling bath; and a control unit controlling the pump, the control unit programmed to operate the pump according to a cycle in which the pump is operated at less than maximum to cause the therapy pad temperature to be raised and to conserve a cooling resource within the cooling bath.

26 Claims, 15 Drawing Sheets

(56) References Cited

U.S. PATENT DOCUMENTS

| | | | |
|---|---|---|---|
| 3,892,229 A | 7/1975 | Taylor et al. | |
| 3,901,221 A | 8/1975 | Nicholson et al. | |
| 3,918,458 A | 11/1975 | Nethery | |
| 3,942,518 A | 3/1976 | Tenteris et al. | |
| 3,971,398 A | 7/1976 | Taylor et al. | |
| 3,993,053 A | 11/1976 | Grossan | |
| 3,994,408 A * | 11/1976 | Belitzky | 215/10 |
| 4,013,069 A | 3/1977 | Hasty | |
| 4,030,488 A | 6/1977 | Hasty | |
| 4,149,529 A | 4/1979 | Copeland et al. | |
| 4,156,425 A | 5/1979 | Arkans | |
| 4,186,732 A | 2/1980 | Christoffel | |
| 4,198,961 A | 4/1980 | Arkans | |
| 4,202,325 A | 5/1980 | Villari et al. | |
| 4,206,751 A | 6/1980 | Schneider | |
| 4,207,875 A | 6/1980 | Arkans | |
| 4,253,449 A | 3/1981 | Arkans et al. | |
| 4,259,961 A * | 4/1981 | Hood, III | 607/104 |
| 4,306,747 A | 12/1981 | Moss | |
| 4,311,135 A | 1/1982 | Brueckner et al. | |
| 4,370,975 A | 2/1983 | Wright | |
| 4,375,217 A | 3/1983 | Arkans | |
| 4,396,010 A | 8/1983 | Arkans | |
| 4,453,538 A | 6/1984 | Whitney | |
| 4,501,126 A | 2/1985 | Norton | |
| 4,691,762 A * | 9/1987 | Elkins | A61F 7/02 165/46 |
| 4,694,521 A | 9/1987 | Tominaga | |
| 4,773,494 A | 9/1988 | Anderson | |
| 4,821,354 A | 4/1989 | Little | |
| 4,841,956 A | 6/1989 | Gardner et al. | |
| 4,844,072 A | 7/1989 | French et al. | |
| 4,962,761 A * | 10/1990 | Golden | 607/104 |
| 4,966,145 A | 10/1990 | Kikumoto et al. | |
| 5,022,387 A | 6/1991 | Hasty | |
| 5,109,832 A | 5/1992 | Proctor et al. | |
| 5,174,285 A * | 12/1992 | Fontenot | 607/104 |
| 5,186,163 A | 2/1993 | Dye | |
| 5,218,954 A | 6/1993 | van Bemmelen | |
| 5,241,951 A | 9/1993 | Mason et al. | |
| 5,241,958 A | 9/1993 | Noeldner | |
| 5,261,482 A | 11/1993 | Lomax et al. | |
| 5,263,473 A | 11/1993 | McWhorter | |
| 5,330,519 A | 7/1994 | Mason et al. | |
| 5,383,894 A | 1/1995 | Dye | |
| 5,476,489 A * | 12/1995 | Koewler | 607/104 |
| 5,496,262 A | 3/1996 | Johnson, Jr. et al. | |
| 5,588,955 A | 12/1996 | Johnson, Jr. et al. | |
| 5,626,556 A | 5/1997 | Tobler et al. | |
| 5,647,051 A | 7/1997 | Neer | |
| 5,669,872 A | 9/1997 | Fox | |
| 5,806,335 A * | 9/1998 | Herbert | A61F 7/10 607/114 |
| 5,843,007 A | 12/1998 | McEwen et al. | |
| 5,865,841 A | 2/1999 | Kolen et al. | |
| 5,871,526 A | 2/1999 | Gibbs et al. | |
| 5,951,502 A | 9/1999 | Peeler et al. | |
| 5,980,561 A | 11/1999 | Kolen et al. | |
| 5,989,285 A | 11/1999 | DeVilbiss et al. | |
| 6,007,559 A | 12/1999 | Arkans | |
| 6,080,120 A | 6/2000 | Sandman et al. | |
| 6,086,609 A * | 7/2000 | Buckley | 607/104 |
| 6,129,688 A | 10/2000 | Arkans | |
| 6,290,662 B1 | 9/2001 | Morris et al. | |
| 6,296,617 B1 | 10/2001 | Peeler et al. | |
| 6,358,219 B1 | 3/2002 | Arkans | |
| 6,387,065 B1 | 5/2002 | Tumey | |
| 6,436,064 B1 | 8/2002 | Kloecker | |
| 6,440,093 B1 | 8/2002 | McEwen et al. | |
| 6,447,467 B1 | 9/2002 | Barak | |
| 6,463,612 B1 | 10/2002 | Potter | |
| 6,463,934 B1 | 10/2002 | Johnson, Jr. et al. | |
| 6,478,757 B1 | 11/2002 | Barak | |
| 6,494,852 B1 | 12/2002 | Barak et al. | |
| 6,544,202 B2 | 4/2003 | McEwen et al. | |
| 6,551,348 B1 * | 4/2003 | Blalock et al. | 607/104 |
| 6,589,194 B1 | 7/2003 | Calderon et al. | |
| 6,592,534 B1 | 7/2003 | Rutt et al. | |
| 6,685,661 B2 | 2/2004 | Peled | |
| 6,719,779 B2 * | 4/2004 | Daoud | 607/105 |
| 7,044,924 B1 | 5/2006 | Roth et al. | |
| 7,063,676 B2 | 6/2006 | Barak et al. | |
| 7,191,798 B2 | 3/2007 | Edelman et al. | |
| 7,207,959 B1 | 4/2007 | Chandran | |
| 7,211,104 B2 * | 5/2007 | Edelman | 607/104 |
| 7,282,038 B2 | 10/2007 | Gillis et al. | |
| 7,354,410 B2 | 4/2008 | Perry et al. | |
| 7,354,411 B2 | 4/2008 | Perry et al. | |
| 7,637,879 B2 | 12/2009 | Barak et al. | |
| 7,640,764 B2 * | 1/2010 | Gammons et al. | 62/259.3 |
| 7,641,623 B2 | 1/2010 | Biondo et al. | |
| 7,658,205 B1 | 2/2010 | Edelman et al. | |
| 7,694,693 B1 | 4/2010 | Edelman et al. | |
| 7,708,707 B2 | 5/2010 | Cook et al. | |
| 7,819,829 B1 | 10/2010 | Chandran | |
| 7,862,525 B2 | 1/2011 | Carkner et al. | |
| 7,871,387 B2 | 1/2011 | Tordella et al. | |
| 7,896,823 B2 | 3/2011 | Mangrum et al. | |
| 7,909,783 B2 | 3/2011 | Mayer et al. | |
| 7,909,861 B2 | 3/2011 | Balachandran et al. | |
| 7,931,606 B2 | 4/2011 | Meyer | |
| 7,942,838 B2 | 5/2011 | Farrow | |
| 7,959,588 B1 | 6/2011 | Wolpa | |
| 7,967,766 B2 | 6/2011 | Ravikumar | |
| 8,613,762 B2 * | 12/2013 | Bledsoe | A61F 7/02 165/46 |
| 2008/0058911 A1 | 3/2008 | Parish et al. | |
| 2008/0077063 A1 | 3/2008 | Meyer et al. | |
| 2009/0069731 A1 | 3/2009 | Parish et al. | |
| 2009/0124944 A1 | 5/2009 | Ravikumar | |
| 2009/0293887 A1 | 12/2009 | Wilkes et al. | |
| 2009/0299249 A1 | 12/2009 | Wilkes et al. | |
| 2009/0299255 A1 | 12/2009 | Kazala et al. | |
| 2009/0299256 A1 | 12/2009 | Barta | |
| 2009/0299257 A1 | 12/2009 | Long et al. | |
| 2009/0299307 A1 | 12/2009 | Barta et al. | |
| 2009/0299308 A1 | 12/2009 | Kazala et al. | |
| 2009/0299340 A1 | 12/2009 | Kazala et al. | |
| 2009/0299341 A1 | 12/2009 | Kazala et al. | |
| 2009/0299342 A1 | 12/2009 | Cavanaugh et al. | |
| 2010/0030306 A1 | 2/2010 | Edelman et al. | |
| 2010/0100017 A1 | 4/2010 | Maguina | |
| 2010/0137764 A1 | 6/2010 | Eddy | |
| 2010/0210982 A1 | 8/2010 | Balachandran et al. | |
| 2010/0249679 A1 | 9/2010 | Perry et al. | |
| 2011/0015587 A1 | 1/2011 | Tumey et al. | |
| 2011/0015589 A1 | 1/2011 | Svedman et al. | |
| 2011/0015590 A1 | 1/2011 | Svedman et al. | |
| 2011/0015593 A1 | 1/2011 | Svedman et al. | |
| 2011/0077723 A1 | 3/2011 | Parish et al. | |
| 2011/0082401 A1 | 4/2011 | Iker et al. | |
| 2011/0092927 A1 | 4/2011 | Wilkes et al. | |
| 2011/0093050 A1 | 4/2011 | Damkoehler | |
| 2011/0152796 A1 | 6/2011 | Kazala, Jr. et al. | |
| 2011/0166480 A1 | 7/2011 | Mayer et al. | |
| 2011/0178481 A1 | 7/2011 | Locke et al. | |
| 2011/0190675 A1 | 8/2011 | Vess | |
| 2011/0196269 A1 | 8/2011 | Arkans | |
| 2011/0257573 A1 | 10/2011 | Hong et al. | |
| 2011/0275983 A1 | 11/2011 | Quisenberry et al. | |
| 2012/0158103 A1 | 6/2012 | Bledsoe | |

FOREIGN PATENT DOCUMENTS

| | | |
|---|---|---|
| EP | 2275165 | 1/2011 |
| IE | S950163 | 12/1995 |
| WO | WO2009/158131 | 12/2009 |
| WO | WO2011/090986 | 7/2011 |

OTHER PUBLICATIONS

Orthofix International, "Orthofix International Introduces FUSION Lateral OA Brace With New Low-Profile Hinge," News Blaze,

(56) References Cited

OTHER PUBLICATIONS published Dec. 4, 2009, http://newsblaze.com/story/2009120405052100002.bw/topstory.html.
Breg Incorporated, "Fusion OA," published 2009, http://www.breg.com/knee-bracing/oa/fusion-oa.html.
Bledsoe Brace Systems, "Bledsoe Cold Control," published 2008, http://bledsoebrace.com/products/cold_control.asp.

\* cited by examiner

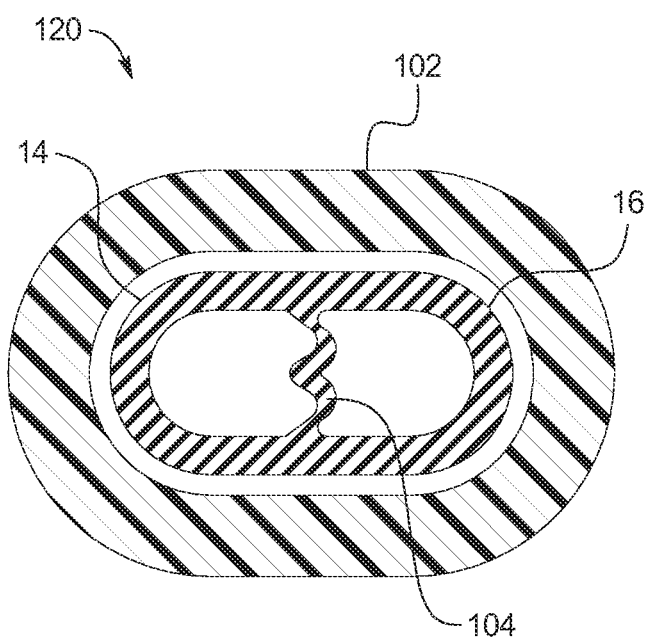

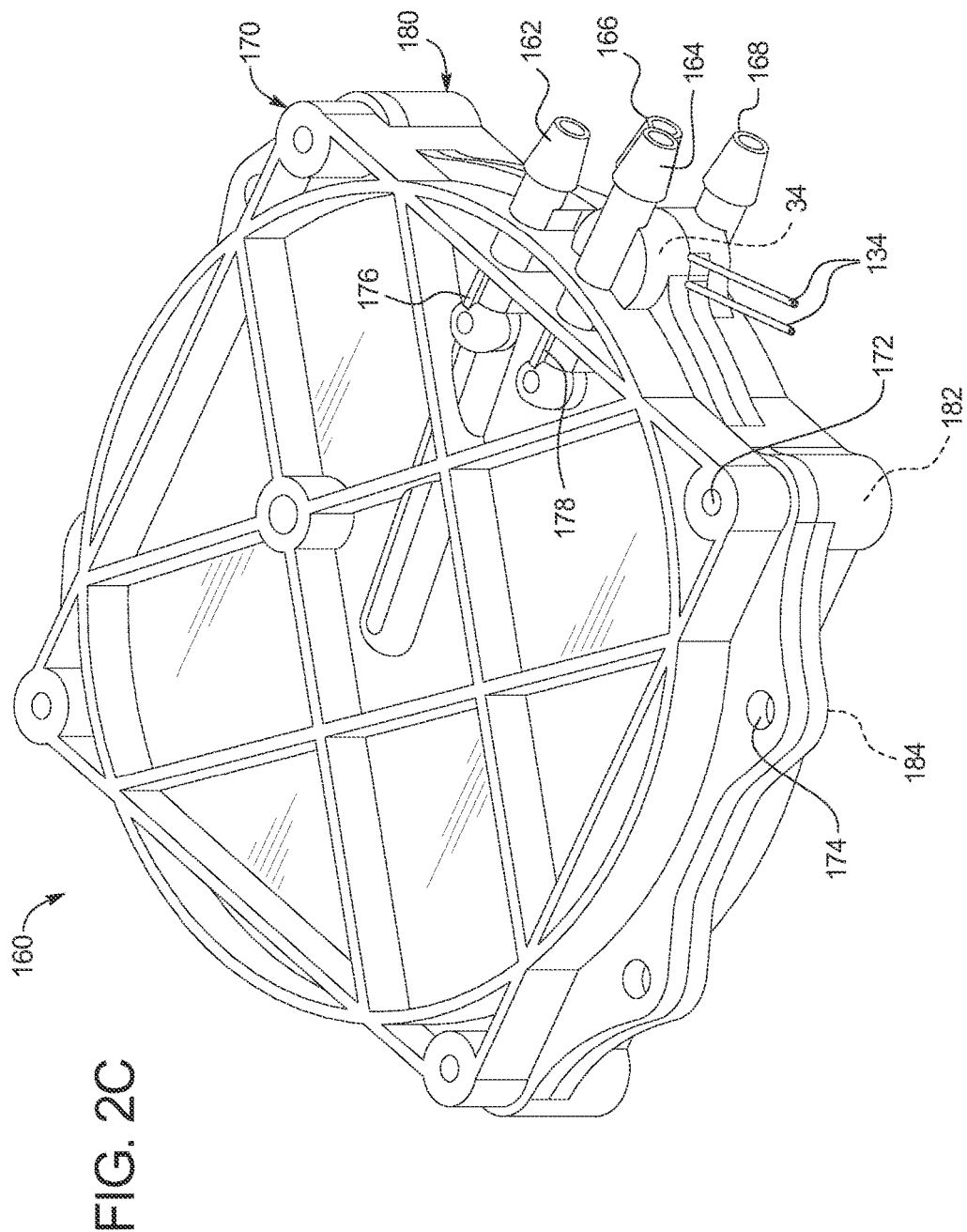

COLD THERAPY SYSTEMS AND METHODS

CROSS-REFERENCE TO RELATED APPLICATION

This application is commonly owned with and related in subject matter to application Ser. No. 12/973,476 ("the '476 application"), entitled, "Cold Therapy Apparatus Using Heat Exchanger", filed Dec. 20, 2010, and issued as U.S. Pat. No. 8,613,762 on Dec. 24, 2013. The entire contents of the '476 application are incorporated herein by reference and relied upon.

BACKGROUND

The present disclosure relates generally to orthopedics and in particular to the therapeutic cooling or heating of a sore or injured body part.

It is known to use chilled water to cool and sooth a sore or injured body part. For example, U.S. Pat. Nos. 5,241,951 and 5,330,519 describe a cold therapy unit that uses chilled water. The patents call for a variable flow restrictor for temperature control. The more the flow restrictor is restricted, the less water flows through the cooling pad, resulting in a higher therapy pad temperature. The less the flow restrictor is restricted, the more water flows through the cooling pad, resulting in a lower therapy pad temperature.

While known devices have provided therapeutic cooling, the devices have had certain drawbacks. For instance, temperature control for certain of these devices has been difficult, leading to instances in which water has been chilled to a level that is uncomfortable for the patient. Also, certain devices cause the ice to melt too quickly, expending the thermal potential of the device. Further, it is desirable to ensure that the water delivered to the cooling pad is not uncomfortably cold.

Still further, with certain cold therapy units, the patient is required to fill a bath with ice and water. This filling can be an area of complaint, especially when the duration of the ice bath is diminished due to overcooling and melting the ice too quickly. Here, the user needs to ambulate and replace the ice frequently to continue therapy, which is often performed immediately after surgery when cooling is most required and moving is most difficult. A need accordingly exists for an improved system and method for the use of ice water baths.

SUMMARY

The present disclosure sets forth a number of features to address the above-described problems with current cold therapy units. One feature is to regulate a pump and/or valve of the unit to cycle therapy pad temperatures between lower and higher therapy temperatures. Another feature is the addition of feedback and the use of feedback to control a valve, which helps to maintain a desired temperature. A further feature is to provide a cooling bath that is easier to use, reducing the ambulatory burden on the user. Besides the pump, valve and the cooling bath, which submerges the liquid or water pump, the primary components of the cold therapy system can also include a control unit, a patient therapy pad and a heat exchanger. Each of these items is discussed in detail herein. In one embodiment, the tubes running from the therapy pad to the heat exchanger and back are pressed against each other inside of an insulating sleeve to promote heat transfer between the tubes. The additional heat transfer can reduce the size of the heat exchanger and potentially eliminate same.

As mentioned, it is contemplated to automatically alternate the temperature of the water to the therapy pad in one embodiment, which can increase the longevity of the ice in the cooling bath. Extending the therapeutic cooling time and delaying the need to refresh the ice in the cold therapy system is advantageous because the patient or user can avoid having to move about.

There are at least two ways that the therapy pad temperature of the present disclosure can be alternated or cycled. In one way, the therapy pad temperature is changed or alternated by changing or alternating the speed of the liquid or water pump, which can be done by controlling the duty cycle of the pump. In another embodiment, if a heat exchanger is used, the therapy pad temperature can be changed or alternated by changing or alternating the amount of water returning from the therapy pad that passes through the heat exchanger to the cooling bath versus water that returns directly to the cooling bath.

In one example using pump duty cycle control, the control unit may be programmed to control the liquid pump to pump for thirty seconds, turning the pump off for thirty seconds, and repeating every minute, resulting in a fifty percent duty cycle. The ice in the cooling bath lasts longer because the average heat loss from the patient to the cooling bath is less than if the pump is operated continuously. And, the patient still receives a desired cooling pad temperature, e.g., 43° F. (6.1° C.), over the fifty percent duty cycle.

In another implementation, if the water temperature falls below a predetermined "low" set point, a microcontroller reduces the water pump speed a first time. If, after a predetermined time period, the water temperature remains too low, the microcontroller further reduces the pump speed a second time, and so on. If this "check-and-reduce-speed" cycle continues for a predetermined number of cycles, the system alerts and/or shuts down for the safety of the patient. In this implementation, the system and method attempt to maintain pump speed as high as possible, while holding the therapy pad temperature to a safe level.

The duty cycle can be controlled to any desired percentage, for example, anywhere from twenty percent to one hundred percent. The percentage can be set automatically or be user set. The resulting therapy pad temperature profile may start for example at 43° F. (6.1° C.), warm to 50° F. (10.0° C.), and return to 43° F. (6.1° C.), over the one minute cycle. The temperature profiles can include ramps, plateaus, asymmetry, and be open loop or closed loop.

The duty cycle change does not have to be an on/off type of change and can instead be a high flow/low flow duty cycle in which the control unit changes the speed of the liquid pump. High flow/low flow duty cycle fluctuation maintains at least some pressure in the therapy pad at all times.

As mentioned above, if a heat exchanger is provided, another system and method for alternating the water temperature is to use a valve to controllably close off or restrict a line that bypasses the heat exchanger (or alternatively the line to the heat exchanger). The valve can be an inline solenoid valve, a pinch-type valve or occluder applied to the tubing, for example. Passing less water through the heat exchanger means that cooling water from the cooling bath remains colder and therefore that the therapy pad temperature remains colder. Here, ice in the cooling bath is used more quickly because the more warm water is returned to the cooling bath. Passing more water through the heat exchanger means that the water from the cooling bath becomes warmer and therefore that the therapy pad temperature becomes warmer. Here, the ice lasts longer because the water returning to the cooling bath is colder after having passed through the heat exchanger. The varying bypass valve method also maintains pressure in the therapy pad at all times.

Timing the alternating cooling cycles can be performed via an electronic timer in a microprocessor of the control unit. Alternatively, the timer is an electromechanical timer. One example electromechanical apparatus and method of timing the on versus off cycles of the valve that controls the heat exchanger bypass line includes the use of a gear-driven rotor. A slowly rotating water powered rotor rotates to trigger an electrical switch that operates a solenoid valve. A purely mechanical timer uses the rotating rotor to operate a mechanical valve.

Thus either the pump or the valve can be used to alternate pad temperature. Further alternatively, a hybrid pump and valve method can be used. In any of these scenarios, control can be completely on versus off or be via proportioned control, e.g., via variable drive current to vary pump speed or via a variable proportioning valve that allows a percentage open of the valve to be varied. Any of these four scenarios can be run open loop or through the use of temperature feedback.

Water temperature can be measured in the lines leading to or from the therapy pad, for example, in front of the therapy pad, downstream of the therapy pad, or via a combination of the multiple temperature readings processed as an average or difference. The temperature readings are fed to the microcontroller that uses the readings for any one or more of (i) reading out to the patient, (ii) using for alarm purposes, and/or (iii) using as feedback to control the duty cycle (on/off or high flow/low flow or valve switching) as just discussed.

Refilling the cooling bath with ice can be a cumbersome chore for the patient, especially after surgery. And if the patient runs out of ice, therapy cannot be continued for a prolonged period. The present system and method contemplate the use of an ice bottle or ice container to improve cooling bath ease of use and therapy longevity. Multiple bottles or containers are provided in one embodiment. The user fills each container with water and freezes the containers prior to therapy. The containers may be provided in pairs that increase surface area contact with water in the bath. The patient could for example be provided with three container pairs, in which the user uses one pair, while a second pair is already frozen and ready to be used and a third pair is currently being frozen. The patient rotates the pairs for continuous use if needed, removing the dependency of producing or buying free ice. The container system also frees the patient from having to dump melted ice water from the reservoir to provide room for fresh ice.

In one embodiment, the containers of the container pair interlock with one another. A carrier is provided that allows the patient to press and turn the carrier onto the interlocked containers and transport the containers from the freezer to the cooling bath or from the cooling bath to the freezer. Once at the cooling bath or freezer, the patient places the carrier and the container pair as an assembly into the cooling bath or freezer. The assembly completes the top of the cooling bath and can be locked to the lower housing of the cooling bath to transport the entire bath. When the ice melts in the bath, the patient removes the assembly, then removes the carrier from the melted containers, and connects the carrier to new frozen container. In this manner, the patient can transport the ice containers easily without having to actually contact the cold containers.

It is accordingly an advantage of the present disclosure to provide a cold therapy unit with improved therapy pad temperature control.

It is another advantage of the present disclosure to provide a cold therapy unit that cools the user safely.

It is a further advantage of the present disclosure to provide a cold therapy unit that prevents a therapy pad temperature from becoming too low.

It is yet another advantage of the present disclosure to provide a cold therapy unit to automatically raise the temperature of the therapy pad by reducing the water flow or by warming the water to the pad.

It is yet a further advantage of the present disclosure to provide a cold therapy unit that uses ice for cooling but does not require the preparation of free ice or the purchase of ice.

It is still another advantage of the present disclosure to provide a cold therapy unit that uses ice for cooling but does not require the patient to empty used ice water to prepare a new cooling bath.

It is still a further advantage of the present disclosure to provide a cold therapy unit that uses ice for cooling and allows ice containers to be readily transported without having to touch the cold containers directly.

Additional features and advantages are described herein, and will be apparent from the following Detailed Description and the figures.

BRIEF DESCRIPTION OF THE FIGURES

FIG. 2A is a sectioned view of one embodiment of a heat exchanging exchanger-pad and pad-exchanger water line useable with the cold therapy systems and methods of the present disclosure.

FIG. 2C is a perspective view of one embodiment of a spiral heat exchanger for mounting to a housing of a cooling bath of the present disclosure.

DETAILED DESCRIPTION

Flow Regimes

Figure 1:
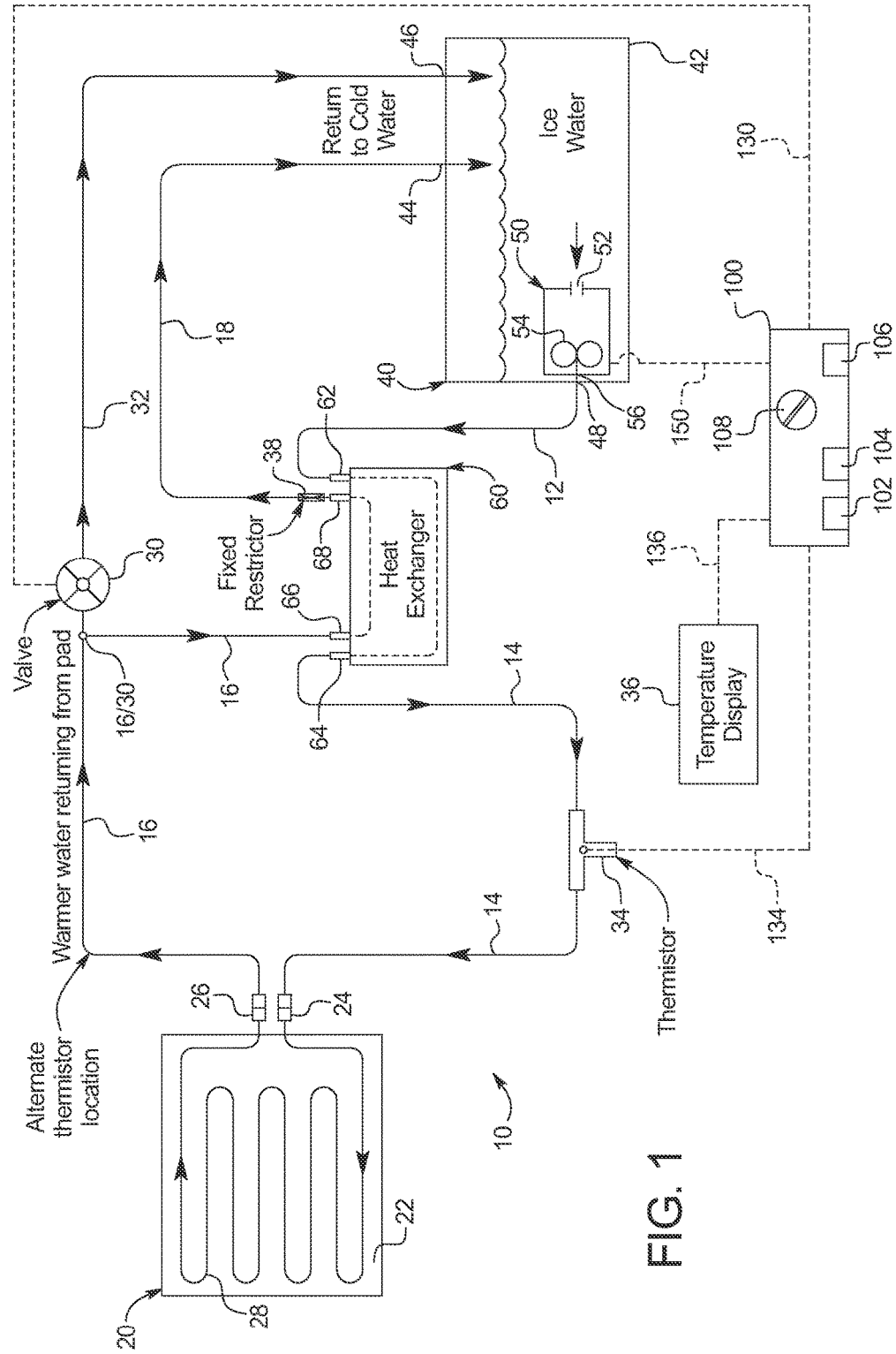
FIG. 1 is a schematic view of one embodiment of a cold therapy system of the present disclosure.

Referring now to the drawings and in particular to FIG. 1, one embodiment of a cold therapy system of the present disclosure is illustrated by System 10. System 10 is numbered generally the same as the numbering provided in the '476 application. Here, like in the incorporated '476 application, primary components of system 10 include a therapy pad 20, a cooling bath 40 and a heat exchanger 60. A bath-exchanger pathway 12 extends from a bath outlet 48 of cooling bath 40 to a chilled water inlet 62 of heat exchanger 60. An exchanger-pad pathway 14 extends from chilled water outlet 64 of heat exchanger 60 to a pad inlet connector 24 of patient pad 20. A pad-exchanger pathway 16 extends from pad outlet connector 26 to heated water inlet 66 of heat exchanger 60. An exchanger-bath pathway 18 extends from a heated water outlet 68 of heat exchanger 60 to a heat exchanger return inlet 44 of cooling bath 40.

Therapy pad 20 includes a patient wrap 22, which is described in the '476 application and incorporated herein by reference. In an embodiment, patient cooling pathway 28 is a serpentine section of tubing, such as the tubing for passageways 14 and 16. Alternatively, patient cooling pathway 28 is a serpentine pattern welded via the multiple plies of patient wrap 22, so as to communicate fluidly with path inlet connector 24 and pad outlet connector 26. In any case, chilled fluid from cooling bath 40 and heat exchanger 60 flows through pad inlet connector 24, through patient cooling pathway 28 to thereby cool the patient and absorb heat from the patient, through pad outlet connector 26, through heat exchanger 60 and returning to cooling bath 40.

Cooling bath 40 includes a housing 42 that is made of a thermally insulating plastic as described in the '476 application and incorporated herein by reference. A liquid pump 50 is submerged beneath a volume of ice-chilled water that is filled within bath housing 42. Liquid pump 50, which is described in the '476 application and incorporated herein by reference, includes a pump inlet 52, a pump motor 54 and a pump outlet 56. In the illustrated embodiment, pump outlet 56 communicates fluidly with bath outlet 48, which in turn communicates fluidly with bath-exchanger pathway 12 running to heat exchanger 60.

In the illustrated embodiment, a fixed restrictor 38 as described in the '476 application and incorporated herein by reference is placed in exchanger-bath pathway 18 just downstream of warmed water outlet 68 of heat exchanger 60. Fixed restrictor 38 creates a back-pressure in pad-exchanger pathway 16 and accordingly in the patient's cooling pathway 28, so as to help inflate patient cooling pathway 28 located within patient wrap 22 of therapy pad 20. In an alternative embodiment, fixed restrictor 38 is not provided, which lessens the workload on pump 50.

Liquid pump 50 pumps ice water from bath housing 42 through bath-exchanger pathway 12 into the cooling section or compartment of heat exchanger 60. The ice water absorbs heat from the warmed water returning from therapy pad 20 through pad-exchanger pathway 16. Slightly heated, chilled water then exits heat exchanger 60 via chilled water outlet 64 and flows through exchanger-pad pathway 14 into therapy pad 20. The slightly warmed-up chilled water flowing through patient cooling pathway 28 of therapy pad 20, inflated via restrictor 38, cools the patient, absorbing heat from the patient, and exits pad outlet connector 26 as warmed water.

System 10 of FIG. 1 includes a diverter valve 30 and a diverter-bath or bypass branch 32 extending in parallel with exchanger-bath pathway 18 to cooling bath 40. As illustrated in FIG. 1, water returning from therapy pad 20 via pad-exchanger pathway 16 tees at tee 16/30 into a first branch 16 that flows into heat exchanger 60 via warmed water inlet 66 and through a warmed fluid section or compartment of heat exchanger 60. The warmed fluid heats the chilled fluid from bath 40 flowing through the chilled section or compartment of heat exchanger 60, such that warmed fluid entering through inlet 66 is cooled slightly before leaving warmed water outlet 68 and flowing through exchanger-bath pathway 18 and heat exchanger return inlet 44 of bath housing 42 into the ice water of cooling bath 40.

A second branch from tee 16/30 flows through diverter-bath pathway or bypass branch 32 via diverter valve 30 directly into cooling bath housing 42, bypassing heat exchanger 60. It should be appreciated that water returning through bypass branch 32 is warmer than water returning to bath housing 42 via exchange-bath pathway 18, because the water returning to bath housing 42 via bypass branch 32 does not give up heat in heat exchanger 60. The cycle just described is run continuously and for as long as the user desires and/or there is a sufficient temperature gradient between therapy pad 20 and cooling bath 40.

System 10 includes a temperature sensor 34, which can be a thermistor or thermocouple, and which outputs to display 36. Temperature sensor outputs to control unit 100.

As described in the '476 application and incorporated herein by reference, diverter valve 30 is a two-way restricting valve that either opens or closes flow to bypass return branch 32 depending upon which way the user or patient turns a dial or knob associated with diverter valve 30. It should be appreciated that regardless of the setting of diverter valve 30, the overall flowrate of water returning to bath housing 42 via return branches 18 and 32 does not collectively vary. In an alternative embodiment, diverter valve 30 is placed instead in pad-exchanger branch 16 downstream of tee 16/30. In still another alternative embodiment, tee 16/30 is replaced with a three-way valve (not illustrated). Here, the manual manipulation of the valve 30 proportions an amount of water returning through bypass branch 32 versus pad-exchanger branch 16.

Open Loop Control

System 10 includes a control unit 100. Control unit 100 can include processing 102, memory 104 and a power supply 106. In the illustrated embodiment, power supply 106 powers liquid pump 50, temperature display 36 and valve 30 (if an automated solenoid valve versus a manual valve). A plug is placed at the inlet side of power supply 106 and accepts a power cord running to the patient's house power. If diverter valve 30 is a manual valve instead of an electric valve, the manual control for diverter valve 30 can also be located at control unit 100.

Electrical lines, which can be power and/or signal lines, are shown dashed. An electrical line(s) 134 extend(s) between control unit 100 and temperature sensor 34. An electrical line(s) 136 extend(s) between control unit 100 and temperature display 36. An electrical line(s) 150 extend(s) between control unit 100 and liquid pump 50. An electrical line(s) 130 extend(s) between control unit 100 and valve 30, if so automated.

While microprocessor 102 and memory 104 are provided in one embodiment, certain methods and corresponding structures may be controlled without needing computer control. For example, the switching of flow states may be performed by an electromechanical timer, such as a timer similar to lighting times used for residential lighting. The electromechanical timer can include a gear-driven rotor that makes and breaks mechanical switches. Or, a purely mechanical, water powered rotor may be used, as water pressure turns the rotor, electrical switches are made and broken. Any of these structures may be used in place of processor 102 and memory 104, for example in the on/off open loop control of pump 50 or valve 30.

The present disclosure contemplates a plurality of ways to ensure that the temperature in therapy pad 20 does not become too cold and to preserve ice or cooling potential. In one embodiment, system 10 automatically alternates the temperature of the water in therapy pad 20 to maintain a safe temperature and to increase the longevity of the cooling potential within the cooling bath 40. In one implementation, control unit 100 changes the speed of water pump 50 to cycle the temperature of therapy pad 20. Changing the speed of water pump 50 changes the amount of water returning through pad-exchanger pathway 16 that passes through heat exchanger 60. It should be appreciated that in this implementation, diverter valve 30 and bypass branch 32 are not necessary but could still be provided if desired.

Control unit 100 and water pump 50 could be cycled in an on-off or duty cycle manner, for example, with water pump 50 running for a certain percentage of the time and stopped completely for the remaining percentage of the time. Here, water either flows though therapy pad 20 at a constant speed or does not flow through therapy pad 20 at all. A single speed pump may be used, in which drive current from control unit 100 to pump 50 is constant when applied.

The resulting temperatures in therapy pad 20 are provided in an open loop manner, meaning there is no feedback to fine tune the temperature to a desired number. An example open-loop cooling cycle can include a desired cold temperature of 43° F. (6.1° C.) at therapy pad 20, which is warmed to a desired temperature of 50° F. (10° C.) when pump 50 is shut down, and which is returned to the desired cold temperature of 43° F. (6.1° C.), and so on. Control unit 100 can be programmed to control cycle time (low to high, then high to low) to be one minute. It is contemplated for control unit 100 to run a duty cycle that has been empirically determined to achieve the desired temperature profile over a, e.g., one minute, cycle assuming a certain heat transfer load from the patient and a particular average temperature of cooling bath 40.

The actual cycle temperatures will likely not be 43° F. (6.1° C.) and 50° F. (10° C.) but instead be in some range around those numbers. In an embodiment, as long as therapy pad 20 does not drop too low, e.g., below 38° F. (3.3° C.), or climb too high, e.g., above 65° F. (18.3° C.), therapy is allowed to continue even though the desired temperatures of 43° F. (6.1° C.) and 50° F. (10° C.) are not being achieved exactly. If the therapy pad 20 temperature falls outside of a limit, system 10 can shut down, shut down and alarm, alarm only, take evasive measures only, or take evasive measures in combination with alarming. Evasive measures can include (i) control unit 100 not running water pump 50 until the therapy pad 20 temperature rises to a safe level, and (ii) control unit 100 running water pump 50 continuously (disregarding the on/off profile) until the therapy pad 20 temperature falls to a useful therapeutic level. The alarm can be an audio alarm and/or be a suitable message displayed on readout 36.

It is contemplated for control unit 100 to store a plurality of therapies, which are differentiated by duty cycle, e.g., "chilly" (pump 50 run sixty percent of the time), "moderate" (pump 50 run fifty percent of the time), or "mild" (pump 50 run forty percent of the time). Control unit 100 can include an input device 108, such as a dial switch, which allows the patient to choose between duty cycle profiles. Input device 108, e.g., the dial, can alternatively have enough adjustability for the user to switch between duty cycles of for example forty percent to sixty percent by single percentage points.

While linear temperature profiles are contemplated in one embodiment, the profiles can include staggered ramps and/or plateaus. The profiles can be symmetrical (e.g., fifty percent on/fifty percent off) or asymmetrical (e.g., sixty percent on/forty percent off). In any case, the ice in cooling bath 40 lasts longer because the average heat loss from the patient to the bath 40 is less than with the pump operating continuously. The patient however still receives the low temperature (e.g., 43° F. (6.1° C.)) cooling benefit for some period of time during the cycle.

In an alternative implementation, a variable speed pump 50 is used and controller includes a pump motor driver that can controllably vary the pump speed. With the on/off control version, control unit 100 sends or does not send power to pump 50 to run or not run pump 50. To vary the speed of pump 50, control unit 100 or a motor driver thereof varies the drive current to the motor of pump 50 to vary pump speed. Here again, diverter valve 30 and bypass line 32 are not needed but may be provided if desired. Here, pump 50 does not have to shut off completely but instead can change from a high speed (lower pad 20 temperature) to a low speed (higher pad 20 temperature) and vice versa according to any of the profile types just described. Control unit 100 can be programmed to change the speed of pump 50 (i) by jumps or steps, (ii) linearly, (iii) in an S-curve or soft start leading to a steeper rise or fall, or (iv) any combination of these.

Changing pump speeds changes therapy pad 20 temperature, conserves cooling resources as above but also maintains pressure on the pad throughout the cycle, whereas the on/off control will tend to lose pad pressure when control unit 100 stops pump 50. Duty cycle for the high flow/low flow methodology can be varied the same as for the on/off methodology, e.g., from forty to sixty percent high flow, to sixty to forty percent low flow. In an embodiment, the high flow/low flow methodology runs open loop as described above, where temperature versus flow profiles are developed empirically and predict temperature outcomes based on a standard patient heat transfer load and cooling bath 40 temperature. Profile selections can again be offered to the patient as options via input device 108 under descriptive names, such as, "chilly", "moderate" and "mild".

If the therapy pad 20 temperature falls outside of a limit (e.g., below 38° F. (3.3° C.) or above 65° F. (18.8° C.), system 10 can again shut down, shut down and alarm, alarm only, take evasive measures only, or take evasive measures in combination with alarming. Evasive measures can include (i) control unit 100 not running water pump 50 until the therapy pad 20 temperature rises to a safe level, (ii) and control unit 100 running water pump 50 continuously (disregarding high/low profile) until the therapy pad 20 temperature falls to a useful level. The alarm can be an audio alarm and/or be a suitable message displayed on readout 36.

In an alternative embodiment, control unit 100 of system 10 is programmed to automatically control diverter valve 30. When diverter valve 30 is a manually operated valve, valve 30 can be a needle type liquid valve that the patient manually controls to proportion the amount of fluid returning from pad 20 that is either directed to heat exchanger 60 or allowed to flow directly to cooling bath 40 through bypass line 32. When diverter valve 30 is automated, the valve can be an inline on/off solenoid or pinch-type valve applied to tubing 32. Here, control unit 100 controllably sends or does not send a discrete signal, e.g., 120VAC, 24 VDC or 5 VDC to open or close valve 30. Or when diverter valve 30 is automated, valve 30 can be a variable proportioning valve that is controlled via, e.g., a 4 to 20 mA or 0 to 5 VDC proportional control signal from control unit 100 to the valve.

The more water returning from therapy pad 20 that is run through heat exchanger 60, the more the cooling potential of bath 40 is preserved. One way to look at it is that the more water that is run through heat exchanger 60, the higher the temperature of cooling water entering pad 20 through exchanger-pad pathway 14. As that water temperature gets higher, the heat transferred from the patient is lowered. Less overall heat transferred by the patient results in an overall reduced usage of cooling potential at bath 40.

Control unit 100 can control the on/off duty cycle of valve 30 just like control unit 100 can control the on/off duty cycle of pump 50 as described above. When valve 30 is closed, all water returning from pad 20 is forced through heat exchanger 60 back to cooling bath 40. When control unit 100 energizes valve 30 (assuming a normally closed valve), valve 30 opens and assuming the resistance to bath 40 through heat exchanger 60 and bypass line 32 to be the same, flow splits between the two, causing the temperature of cooling water entering pad 20 through exchanger-pad pathway 14 to be lowered and patient heat transfer to be raised.

On/off duty cycle control of valve 30 can again be run open loop. Duty cycle can be varied anywhere from valve 30 being permanently closed to valve 30 being permanently opened. Profiles can again be offered to the patient for selection via input device 108 under descriptive names, such as, "chilly", "moderate" and "mild", which increasingly close valve 30 to raise the overall cooling temperature. The profiles can be symmetrical, non-symmetrical, constant and/ or varied over time as desired. If the therapy pad 20 temperature falls outside of a limit (e.g., below 38° F. (3.3° C.) or above 65° F. (18.8° C.), system 10 can shut down, shut down and alarm, alarm only, take evasive measures only, or take evasive measures in combination with alarming. Evasive measures can include (i) control unit 100 shutting valve 30 until the therapy pad 20 temperature rises to a safe level, and (ii) control unit 100 keeping valve 30 open continuously (disregarding on/off profile) until the therapy pad 20 temperature falls to a useful level. The alarm can be an audio alarm and/or be a suitable message displayed on readout 36.

Control unit 100 can alternatively control a proportional cycle of valve 30 just like control unit 100 can control the proportional cycle of pump 50 as described above. Here, an elective variable or proportional valve 30 is provided instead of an electric on/off type valve. Proportional valve 30 can be opened and closed (i) by jumps or steps to different percentage open positions, (ii) linearly to a different percentage open position, (iii) in an S-curve or soft start leading to steeper rise or fall to different percentage open positions, or (iv) any combination of these. To vary the percentage open of valve 30, control unit 100 can use a varied analog signal or a digital pulse-width-modulation ("PWM") of the output signal to valve 30. Proportional valve 30 control can again be packaged into discrete profiles selectable by the patient via input device 108. Proportional valve 30 control can again be performed open loop with alarming and/or evasive reaction taken to combat under- and over-temperatures as described herein.

It should be appreciated that under both the on/off and proportional valve 30 methodologies, pad pressure is maintained because the flow to and from therapy pad 20 is not varied.

Closed Loop Control

Four open loop versions of system 10 have just been described, on/off pump 50, proportional pump 50, on/off valve 30 and proportional valve 30. In the open loop system, the reading from temperature sensor or transducer 34 is displayed to the patient at display 36 and is fed into control unit 100, which uses the signal, e.g., for alarm purposes. Control unit 100 does not however use the temperature signal directly for the control of pad 20 temperature.

It is contemplated for control unit 100 to use any of the above four systems but alternatively under closed loop or servo type control. Here, memory device 104 is programmed to store a desired temperature profile for pad 20 temperature. Processor 102 is programmed to retrieve from memory device 104 the desired temperature for any given instant, receive an actual temperature reading from temperature sensor or transducer 34, and make an adjustment if needed to whatever control mechanism (on/off, proportional, pump, valve) that system 10 employs so as to make the actual temperature meet or come closer to the desired temperature in the next sample cycle of processor 102.

With pump on/off, processor 102 can adjust duty cycle so that pump 50 is on more often or off more often in an attempt to adjust actual temperature to meet desired temperature. With pump proportional, processor 102 can adjust the drive current to the motor of pump 50 so that pump 50 pumps faster or slower to adjust actual temperature to meet desired temperature. With valve on/off, processor 102 can adjust duty cycle so that valve 30 is open more often or closed more often in an attempt to adjust actual temperature to meet desired temperature. With valve proportional, processor 102 can adjust the output (e.g., via analog signal or PWM) to valve 30 so that valve 30 is more opened or more closed to adjust actual temperature to meet desired temperature.

The closed loop version of system 10 can alarm and perform alarm evasive maneuvers according to any of the alternative embodiments discussed above for the open loop versions of system 10. The temperature profiles stored by memory device 104 can be of any type discussed herein, including profiles that have temperature jumps or step, profiles that change temperature linearly, profiles that change temperature according to an S-curve or soft start leading to a steeper rise or fall in temperature, profiles that are symmetrical, profiles that are non-symmetrical, profiles that change the same way each cycle or profiles that vary from cycle to cycle.

The feedback systems and methods in one embodiment endeavor to meet a desired pad temperature, be it a lower or higher pad temperature according to a selected temperature profile. In another embodiment, the feedback systems attempt to maintain a certain temperature and also to maximize flowrate. Thus if the current setting is 43° F. (6.1° C.) and the current temperature measured is 43° F. (6.1° C.), which before would signal no change to pump 50 operation, now is taken by control unit 100 as an opportunity to increase flowrate and see if the actual temperature still reads 43° F. (6.1° C.) or within some range thereof. Flowrate is increased until the temperature drops from the set point or drops too far out of range form the set point. At this point, flowrate is decreased in increments until the set point temperature is reached. The cycle is then repeated.

FIG. 1 illustrates different possible locations for temperature sensor 34. The different locations include being in exchanger-pad pathway 14 upstream of pad 20 or being in pad-exchanger pathway 16 downstream of pad 20. In a third embodiment, temperature sensors at both upstream and downstream locations are used for reading out, alarming and/or feedback control. In this third embodiment, the multiple temperatures can be combined or averaged, wherein the combined or averaged signal is used as the feedback signal.

For either the open loop or closed loop versions of system 10, it is contemplated to use a hybrid pump control/valve control system and method. For example, if a sharp change in temperature is needed, control unit 100 can control both pump 50 and valve 30 to react a certain way. For example, if an overtemperature alarm is reached, control unit 100 can command pump 50 to pump continuously (and at a fastest rate if a variable speed pump) and to open valve 30 continuously (and to a most open position if a proportional valve), so that the pad 20 temperature can be brought down to a therapeutically useful temperature as soon as possible.

Heat Exchange Tubing and Associated System

Referring now to FIG. 2A, one embodiment for a thermally insulated heat exchanger line 120 running from therapy pad 20 to heat exchanger 60 is illustrated. Heat exchange line 120 includes an insulating sleeve 102 that houses exchanger-pad pathway 14 and pad-exchanger pathway 16, which can be coextruded together. Sleeve 102 is made in one embodiment of neoprene. Exchanger-pad pathway 14 and pad-exchanger pathway 16 can be made of a plastic material, such as polyvinylchloride ("PVC"), polyurethane, polyethylene, or silicone rubber. Exchanger-pad pathway 14 and pad-exchanger pathway 16 are formed or pressed together, e.g., coaxially, to allow heat to transfer from pad-exchanger pathway 16 to exchanger-pad pathway 14. The heat exchange tubing can be used to reduce the size of heat exchanger 60 and to possibly eliminate the need for same.

As illustrated in FIG. 2A, the openings or lumens for tubes 14 and 16 can be coextruded so as to (i) increase the abutting surface area contact between the warmed (pathway 16) and cold (pathway 14) fluids, and (ii) thin the wall between the warmed and cold fluids. In the illustrated embodiment, wall 104 is extruded to be relatively thin and wavy or corrugated to increase surface area (system 10 is low pressure and pressures should be roughly equal in tubes 14 and 16 so that wall 104 can be thin without rupturing).

In an alternative embodiment, wall 104 can instead be a bendable metal, e.g., aluminum or copper wire, foil, mesh or mesh coating (onto a bendable solid rubber or polymer tube). The foil, mesh or mesh coating could be horizontally disposed as opposed to being vertically disposed as shown in FIG. 2A, so as to (i) increase surface area of the conductive interface and (ii) be bendable along the longer horizontal length of heat exchanger line 120. The metal wire barrier, metal foil barrier, metal mesh barrier or mesh coated barrier 104 blocks flow as before but is a better conductor than a pure polymer or rubber wall, so that heat transfer between pathways 14 and 16 is increased. It is possible here that the outer tubular wall of pathways 14 and 16 be eliminated, and that the metal wire barrier, metal foil, metal mesh barrier or mesh coated barrier 104 be fitted sealingly and directly, e.g., overmolded into, insulating sleeve 102.

Other features contemplated for alternatively or additionally (to above) increasing the heat exchange ability of heat exchanger line 120 include thinning the walls of tubes 14 and 16. Also, the surface area of the material between the lumens of pathways 14 and 16 can be increased to increase convective heat transfer. FIG. 2A shows one example of this, in which wall 104 has an increased surface area with respect to an amount of contact with the lumens of pathways 14 and 16, say, compared to the amount of the same surface area provided if tubes 14 and 16 are connected by point contact. Wall 104 does not have to be serpentine as shown in FIG. 2A to increase the surface area in the manner just described and can instead be linear or curved to form circular lumens. Still further alternatively or additionally, the oblong-shaped structure forming pathways 14 and 16 can be surrounded by a metal or conductive foil (not illustrated). The foil adds a new flow path for heat using a material with higher thermal conductivity than the oblong-shaped structure material.

Figure 2B:
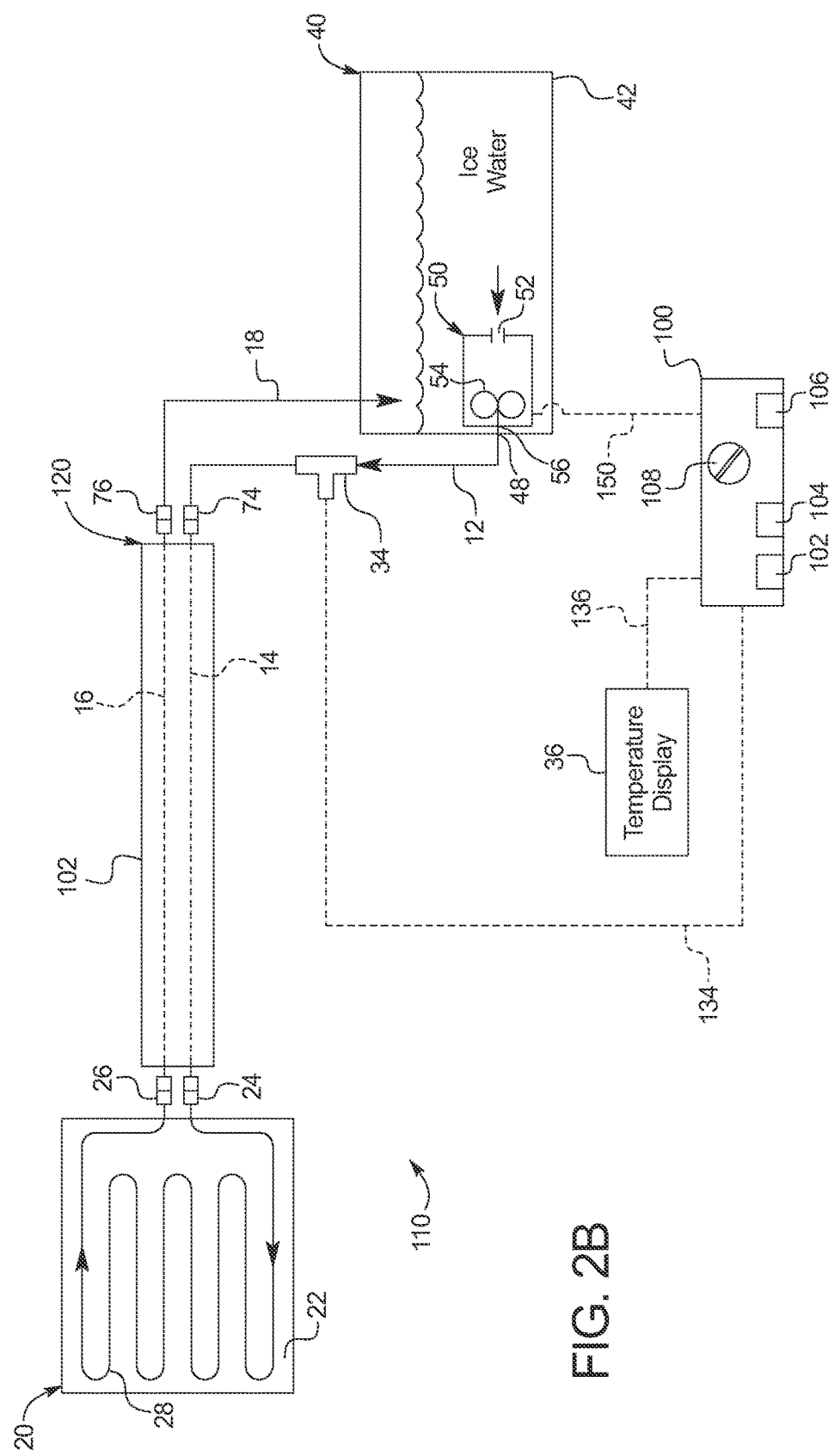
FIG. 2B is a schematic view of a second embodiment of a cold therapy system of the present disclosure that uses the heat exchange tubing of FIG. 2A in place of the heat exchanger shown in FIG. 1.

FIG. 2B illustrates an alternative system 110 of the present disclosure, which replaces heat exchanger 60 of system 10 with heat exchanger line 120 discussed above in connection with FIG. 2A. It should be appreciated that system 110 is simpler than system 10. System 110 in the illustrated embodiment has also eliminated diverter valve 30. As discussed in detail in the '476 application, a system using heat exchanger 60 can also operate without the diverter valve.

For ease of illustration, system 110 is shown operating with a pigtail or short line extending from cooling bath 40. The short line includes bath-exchanger pathway 12 and exchanger-bath pathway 18 as described above. Pathways 12 and 18 extend here instead to exchanger line 120, which has a desired length, e.g., eight feet (2.4 meters). The length of heat exchanger line 120 is chosen to provide a desired amount of heat exchange given an expected amount of heat transfer occurring with the patient at therapy pad 20 and provided at cooling bath 40.

Bath-exchanger pathway 12 connects to heat exchanger line 120 via connector 74, while exchanger-bath pathway 18 connectors to heat exchanger line 120 via connector 76. Connectors 74 and 76 are alternatively bulkhead connectors mated to housing 42 of cooling bath 40, eliminating the need for the short line including bath-exchanger pathway 12 and exchanger-bath pathway 18. On its other end, heat exchanger line 120 connects to therapy pad 20 via connectors 24 and 26 described above for system 10.

Pad 20 and bath 40 include any of the structure and alternatives discussed above for system 10. Control unit 100 likewise includes any of the structure and alternatives discussed above for system 10. Valve 30 is not provided and therefore does not need to be controlled by control unit 100. Temperature sensor 34 is embedded into insulating sleeve 102 and can sense the temperature of either therapy pad inlet line 14 (as is illustrated) or therapy pad outlet line 16. Alternatively, two sensors 34 are provided, one for each line 14 and 16, as has been discussed above. Sensor(s) 34 outputs to control unit 100, which can use the temperature signal for any of the reasons discussed herein. Any of the open loop and closed loop variable speed pump 50 temperature control methods discussed above may be used in connection with system 110. If valve 30 is alternatively provided with system 110, any of the open loop and closed loop on/off or variable orifice valve 30 temperature control methods discussed above may be used in connection with system 110.

Heat Exchanger, Pump Mounting

Each embodiment discussed in connection with FIGS. 3 to 10 of the '476 application regarding the heat exchanger, pump mounting and associated housing is incorporated herein expressly by reference. Referring now to FIG. 2C, one alternative heat exchanger for system 10 is illustrated by spiral heat exchanger 160. Spiral heat exchanger 160 can be mounted to housing 42 of cooling bath 40, which is illustrated and described below in more detail in connection with FIGS. 3 to 14. In one embodiment, spiral heat exchanger 160 is mounted in a horizontal orientation at the front end 142 of housing 42 shown below. Heat exchanger 160 is mounted such that inlets 162 and 166 and outlets 164 and 168 face towards an opening 144 at the front end of housing 42, so that tubes running to and from therapy pad 20 can be readily connected to the heat exchanger. Pump 50 in an embodiment is submerged in housing 42 beneath heat exchanger 160. In an embodiment, pump outlet 56 of pump 50 is connected fluidly to, e.g., directly coupled to, an air separation device (not illustrated), which removes air from the water circulated through spiral heat exchanger 160 and therapy pad 20.

As illustrated in FIG. 2C, spiral heat exchanger 160 includes an upper, to-pad water chamber 170 and a lower, to-bath water chamber 180. Chambers 170 and 180 can be made of a suitable, moldable plastic, such as acrylonitrile butadiene styrene ("ABS"), polyvinylchloride ("PVC"), polyethylene ("PE"), polyurethane, nylon, polycarbonate ("PC"), high density polyethylene ("HDPE"), PE+low density polyethylene ("LDPE") and low-low density polyethylene ("LLDPE"). Chambers 170 and 180 are bolted together at aligned, recessed fastener holes 172 and 182. Chambers 170 and 180 may have internal keying features, such that internal parts, such as gasketing, cannot be inserted incorrectly. Chambers 170 and 180 may have external keying features, such that spiral heat exchanger 160 cannot be mounted incorrectly within housing 42 of cooling bath 40. Chambers 170 and 180 are bolted together to housing 42 via aligned fastener holes 174 and 184.

Upper, to-pad water chamber 170 includes a chilled water inlet 162 and a chilled water outlet 164. Chilled water inlet 162 in the illustrated embodiment leads to a center of the spiral heat exchange chamber. Chilled water from inlet 162 spirals outwardly, around and around, until reaching chilled water outlet 164, after which the "warmed-up" chilled water flows to therapy pad 20. In the illustrate embodiment, temperature transducer or sensor 34, e.g., a thermistor, is sealed between chambers 170 and 180. A sensing head of temperature sensor 34 is o-ring sealed to upper chamber 170 and in contact with the "warmed-up" chilled water exiting chilled water outlet 164. Signal wires 134 lead to control unit 100 as describe above.

Lower, to-bath water chamber 180 includes a heated water inlet 166 and a heated water outlet 168. Heated water inlet 166 in the illustrated embodiment enters through the side of the spiral heat exchange chamber 180. Heated water from inlet 166 spirals inwardly, around and around, until reaching heated water outlet 168, after which the "cooled-down" warm water flows into cooling bath housing 42. The illustrated arrangement places the coldest cold water in counter flow heat exchange communication with the warmest warm water, which is in general the most efficient way to construct heat exchanger 160.

In one embodiment, internal spiral paths of chambers 170 and 180 are sealingly mated so that chilled and warm water each flow within spiral paths that each are bordered by the internal walls of both chambers 170 and 180. Here, there is no central divider and water can flow on both sides of the interface between the two chambers. In an alternative embodiment, there is a divider (not illustrated) between chambers 170 and 180, such that chilled water spirals between upper chamber 170 and the divider, while warmed water spirals between lower chamber 180 and the divider. The divider provides the conductive heat exchange surface area between the chilled and warmed water and can be made, for example, of a conductive material, such as, copper, aluminum, stainless steel and alloys thereof.

Cooling Bath

Figure 3:
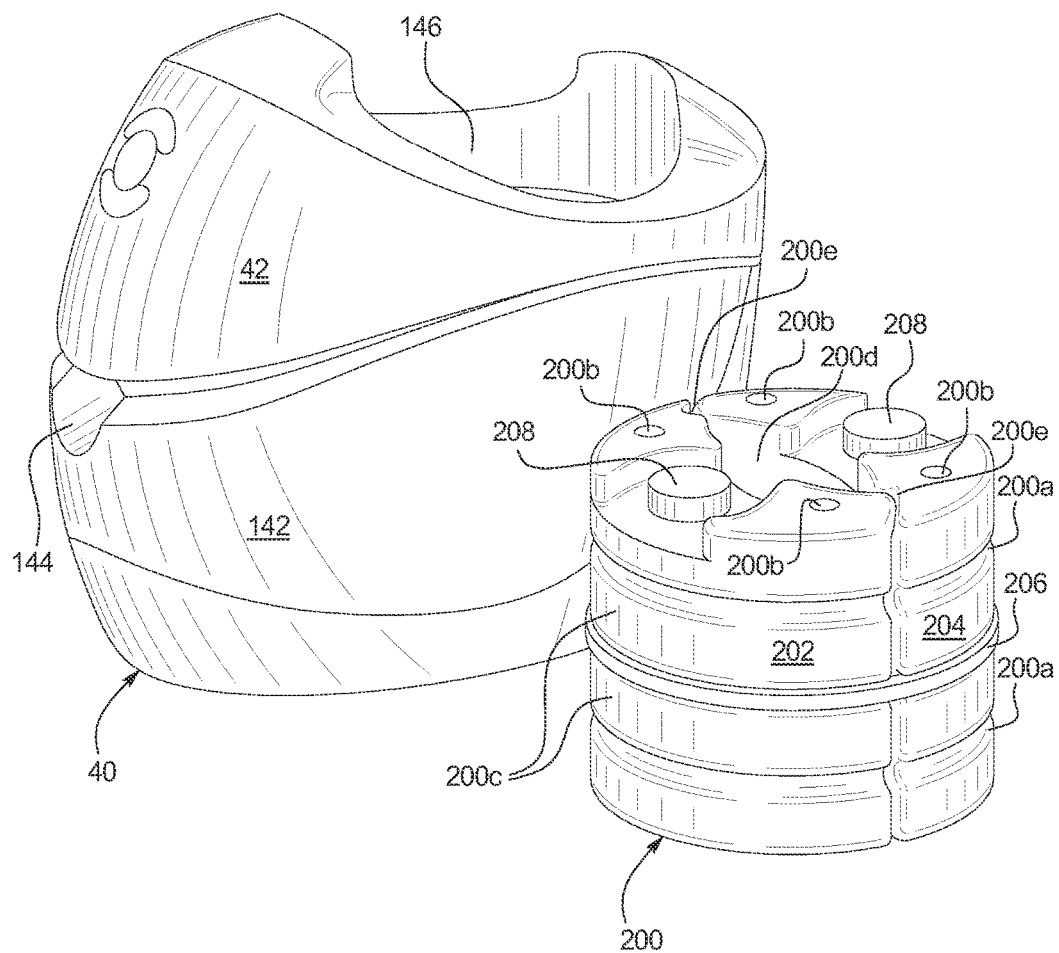
FIGS. 3 to 10 are perspective views of one embodiment of a cooling bath employing a replaceable ice container assembly useable with the cold therapy systems and method of the present disclosure.

Referring now to FIGS. 3 to 14, one embodiment for cooling bath 40 is illustrated. FIG. 3 illustrates that cooling bath 40 includes a housing 42 that is made of a thermally insulating plastic as described in the '476 application and incorporated herein by reference. A liquid pump 50 is submerged at the front end 142 of housing 42. Front end 142 of housing 42 also houses heat exchange 60 as is shown and described in the '476 application. The front end 142 of housing 42 also defines an opening 144 that includes connectors structured and arranged to receive mating connectors located at the end of a line, such as exchanger line 120, running from therapy pad 20, which fluidly and sealingly connect exchanger-pad pathway 14 and pad-exchanger pathway 16 to heat exchanger 60 located inside housing 42 at front end 142. In an alternative construction, the front end 142 of housing 42 defines an opening 144 that instead includes a pigtail or short length of tubing of about one to two feet (30.5 to 61 centimeters) that terminates in connectors structured and arranged to receive mating connectors located at the end of exchanger line 120 running from therapy pad 20. The pigtail or short line fluidly and sealingly splices exchanger-pad pathway 14 and pad-exchanger pathway 16 to heat exchanger 60 located inside housing 42 at front end 142.

In an embodiment, once inside housing 42, pad-exchanger pathway 16 splits into (i) pathway 16 that continues to exchanger 60 and (ii) bypass line 32 that transfers heated fluid directly into cooling bath 40. Thus exchanger line 120 need only have the two lumens 14 and 16 shown and described above in connection with FIG. 2. Again, exchanger line 120 may obviate the need for separate heat exchanger altogether. In such a case, exchanger line 120 can be provided with three lumens, including an additional lumen (for air pressure) that is not in heat exchange relationship with another lumen. Control unit 100 can be placed physically in the exchanger line 120 and house tee 16/30 and valve 30 along with its other components. Opening 144 here includes three fluid tight connectors for receiving exchanger line 120 mating connectors for pathways 14, 16 and the air line (for air pressure).

Liquid pump 50 pulls chilled water from a reservoir area of housing 42 of bath 40. The top of reservoir is provided with a large opening 146. Large opening 146 enables the patient to place water into the reservoir of housing 42. Large opening 146 also enables the patient to place an ice container or bottle assembly 200 into the reservoir of housing 42.

Ice container or bottle assembly 200 in the illustrated embodiment is provided with a pair of containers 202 and 204 that fit together in the illustrated case to form an overall generally cylindrical container. Containers 202 and 204 are made of a polymer material in one embodiment, such as polyvinylchloride ("PVC"), polyethylene ("PE"), polyurethane, nylon, polycarbonate ("PC"), high density polyethylene ("HDPE"), PE+low density polyethylene ("LDPE") and low-low density polyethylene ("LLDPE"). Containers 202 include surface irregularities such as grooves 200a, bores 200b, undulations 200a, protrusions 200c and/or other surface area increasing features that increase water flow, turbulence and the resulting convection heat transfer from the water outside of containers 202 and 204 to the ice inside of the containers. Containers 202 and 204 can interlock together and/or be held together (i) via one or more removable band or strap 206 and/or (ii) via a carrier 210 illustrated below that fits over the mated containers 202 and 204 to hold same together. When interlocked or banded together, containers 202 and 204 in the illustrated embodiment are constructed to leave a pointed oblong three-dimension space or volume 200d for water to flow between the bottles 202 and 204 and between mating features 200e of containers 202 and 204.

Containers 202 and 204 are each fitted with a cap 208 that is removable (e.g., threaded on and off) to allow water to be placed inside the containers. Containers 202 and 204 are then re-capped and placed in a freezer so that the water freezes. When frozen, containers 202 and 204 are ready for use. It is contemplated that system 10 provide multiple pairs of containers 202 and 204, such as three pairs. In this way, one container pair can be in use, a second container pair can be in the freezer, frozen, and immediately ready for use, while the third container pair is in the freezer being frozen. In this manner, ice is continuously provided. The patient's house ice-maker is not relied upon or taxed, and the patient is not required to purchase ice.

It should be appreciated that while frozen ice containers or bottles are used in the illustrated embodiment, it is also contemplated to alternatively use frozen gel-packs that are held together in mesh bags for example. Three such mesh bags of gel-packs can be provided and achieve the same functional rotation that has just been described for ice container assembly 200.

Figure 4:
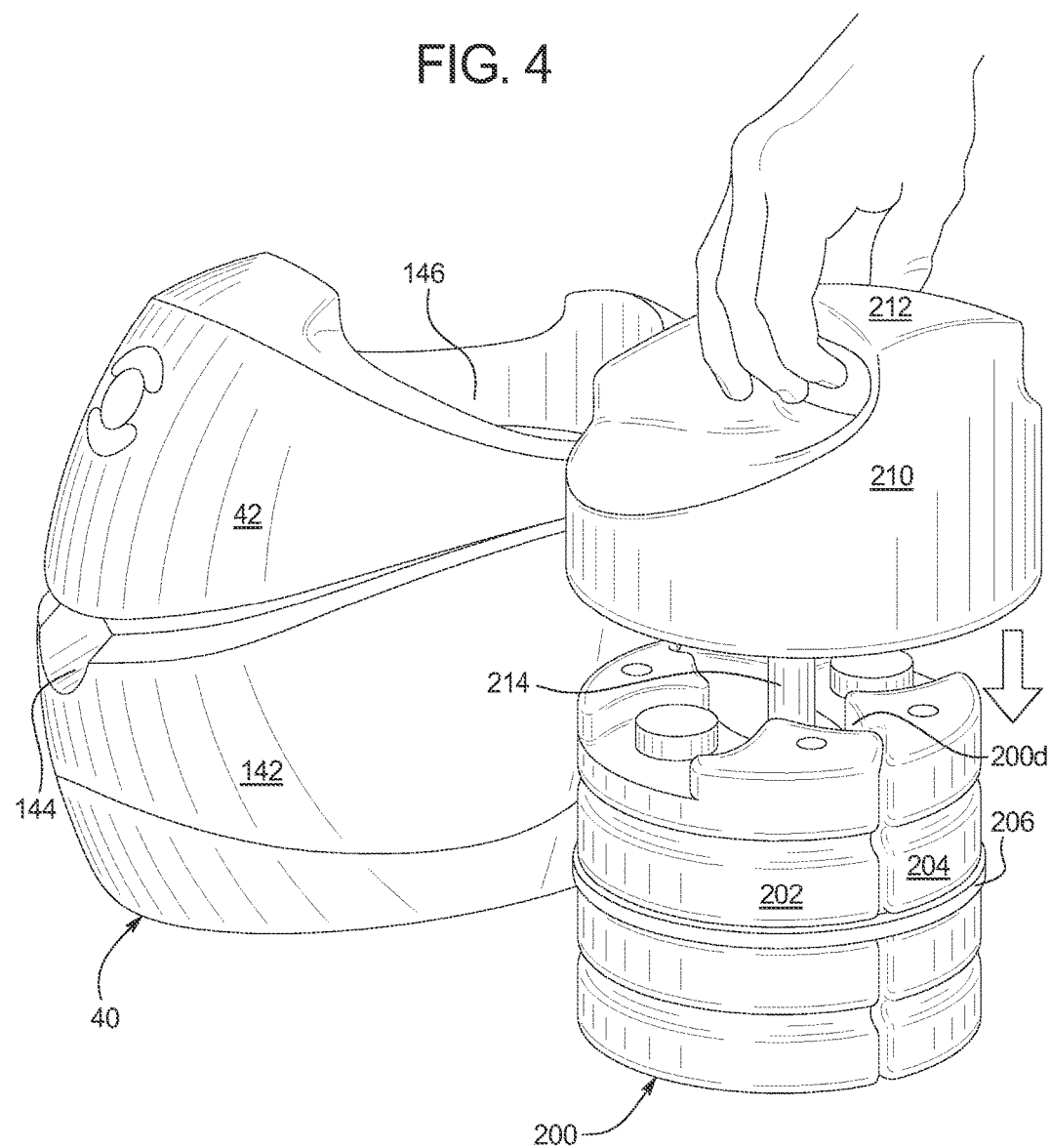
Figure 5:
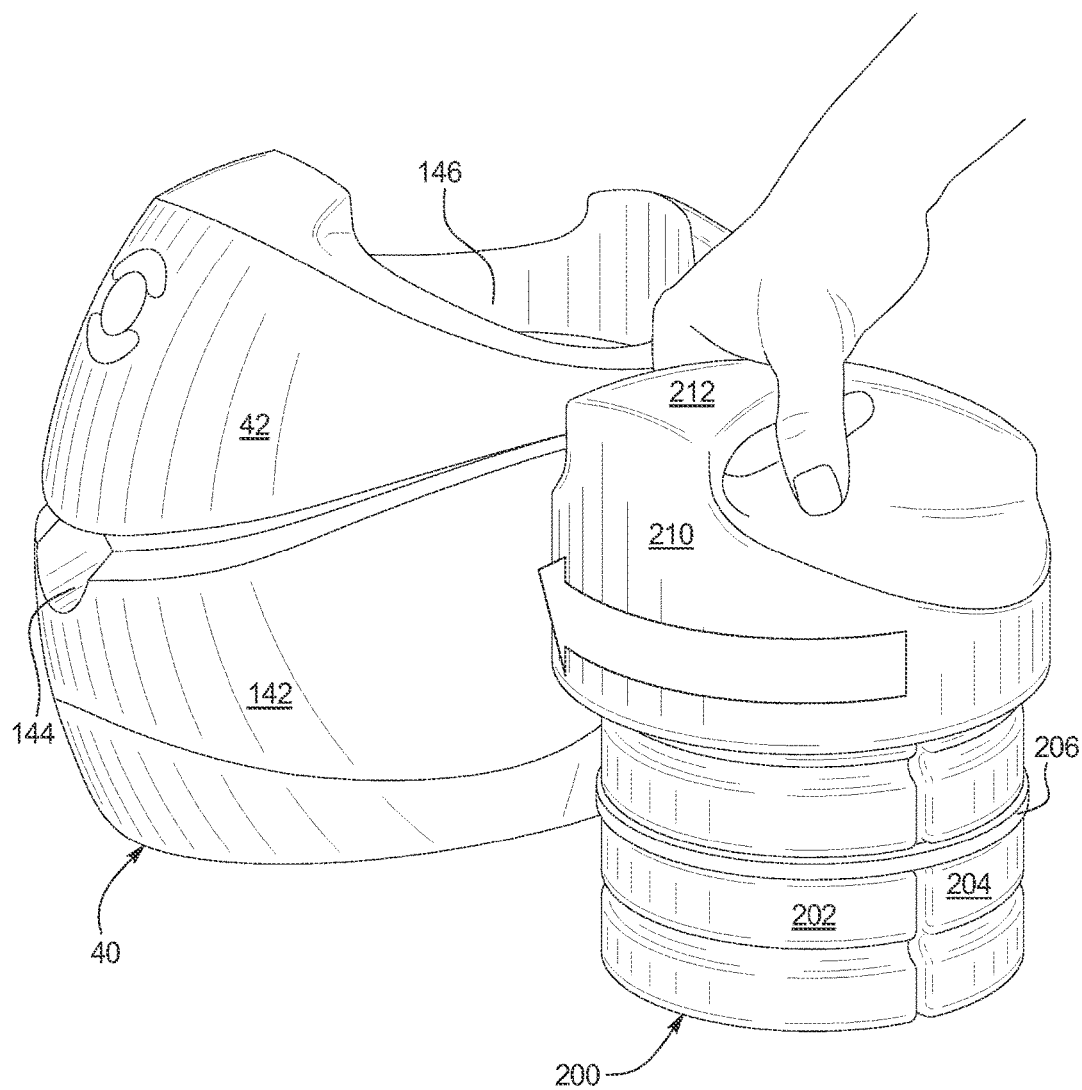
Figure 6:
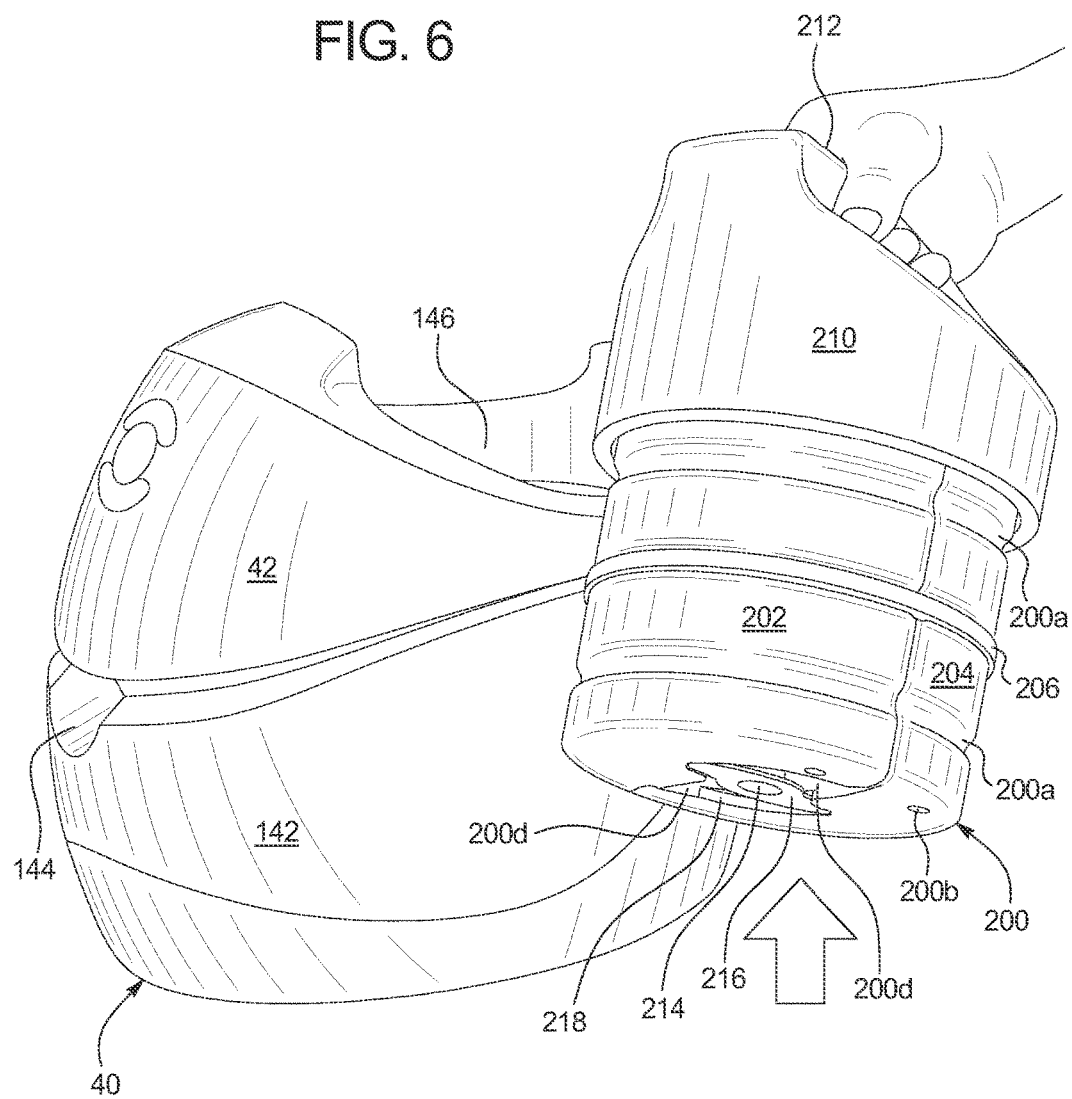

FIG. 4 illustrates that container assembly 200 in one embodiment includes a carrier 210 having a handle 212 structured and arranged for the patient to grasp and lift the carrier 210. Carrier 210 can be made of any of the insulating materials described above for housing 42. The underside of carrier 210 includes a stem 214 having a flange 216 located at the distal end of stem 214 (FIGS. 4 and 6).

When stem 214 is inserted, as indicated by the arrow in FIG. 4, into space 200d between containers 202 and 204, the distal end of stem 214 and flange 216 extend to the bottom of the containers. When the patient presses on and turns carrier 210 clockwise relative to the mated containers 202 and 204, as highlighted by the arrow of FIG. 5, flange 216 rotates beneath a lip 218 (FIGS. 11 and 12) of each container 202 and 204, located on the bottom of the containers (lips 218 not viewable in FIG. 6). In particular, lips 218 are located up from the bottoms of the containers a distance approximately equal to the thickness of flange 216. Pointed oblong space 200d between containers 202 and 204 and flange 216 is sized so that flange 216 can be inserted the full way through the containers. When flange 216 is flush with the bottoms of containers 202 and 204, the patient can rotate handle 212 and flange 216 beneath lips 218 (FIG. 5) to lift assembly 200, including containers 202 and 204 and carrier 210, as illustrated in FIG. 6.

Figure 7:
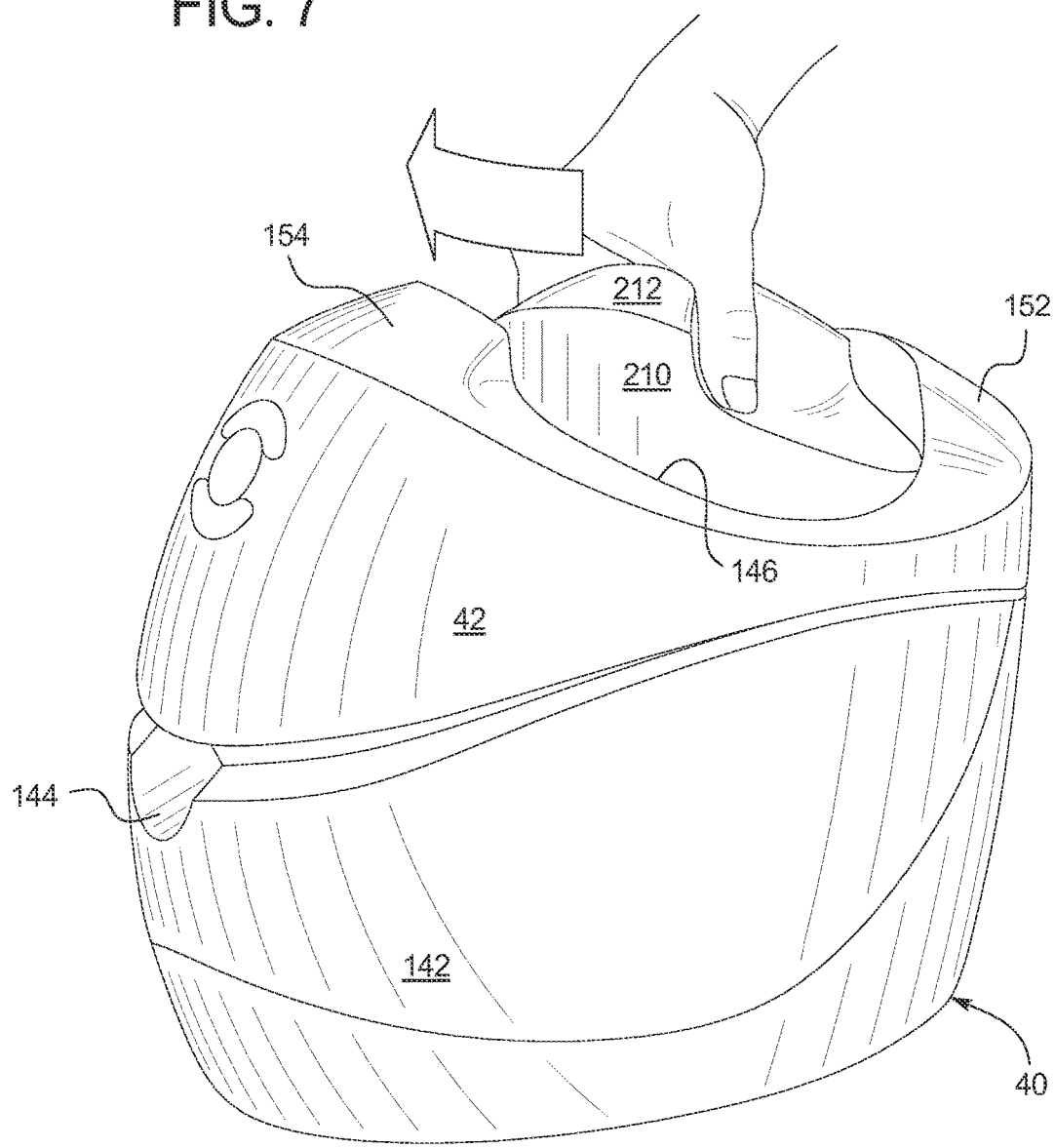

In FIG. 7, the patient inserts the mated carrier 210 and containers 202 and 204 into large opening 146 of housing 42. Containers 202 and 204 extend to the topside of the bottom of housing 42 in one embodiment. The patient rotates handle 212 and container 210 clockwise in FIG. 7, to releasably lock handle 212 and container 210 into housing 42. One suitable structure for locking handle 212 and container 210 into housing 42 is illustrated and discussed in detail below in connection with FIGS. 13 and 14.

After handle 212 is rotated clockwise in FIG. 7, handle 212 and carrier 210 in essence complete the top of housing 42. That is, carrier 210 and handle 212 fill in the piece missing from housing 42 caused by large aperture 146. Handle 212 bridges the contour between rear, top portion 152 and front, top portion 154. Carrier 210 also plugs hole 146 and completes the insulating shell formed around the cold water held within cooling bath 40. After handle 212 is rotated clockwise in FIG. 7, handle 212 can then be used to lift and transport the entire cooling bath 40.

Figure 8:
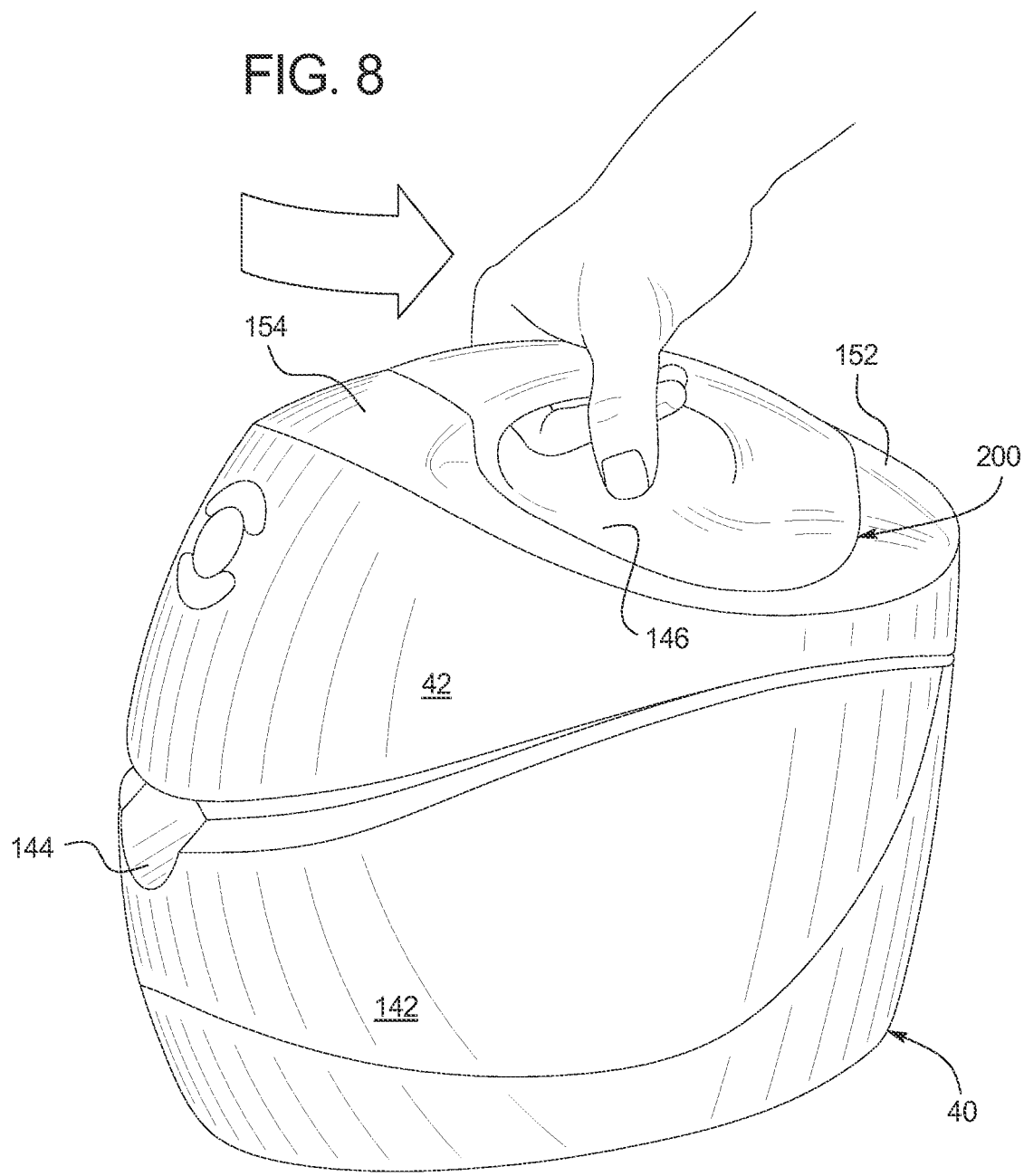

In FIG. 8, when the ice within containers 202 and 204 has melted, the patient turns handle 212 counterclockwise as indicated by the arrow to release the entire assembly 200 from housing 42. In an embodiment, pressing on handle 212 helps to release carrier 210 from containers 202 and 204, but is not needed to release the entire container assembly 200 from housing 42. Thus when the patient just turns handle 212 in FIG. 8 (without pressing the handle), assembly 200 comes free from housing 42 as opposed to carrier 210 coming free from bottles 202 and 204. Alternatively, the weight of the water inside bottles 202 and 204 tends to hold lips 218 against flange 216, such that turning handle 212 counterclockwise in FIG. 8 allows carrier 210 and containers 202 and 204 to turn relative to housing 42 before carrier 210 will rotate relative to containers 202 and 204. Assembly 200 can therefore be removed from housing 42 intact.

Figure 9:
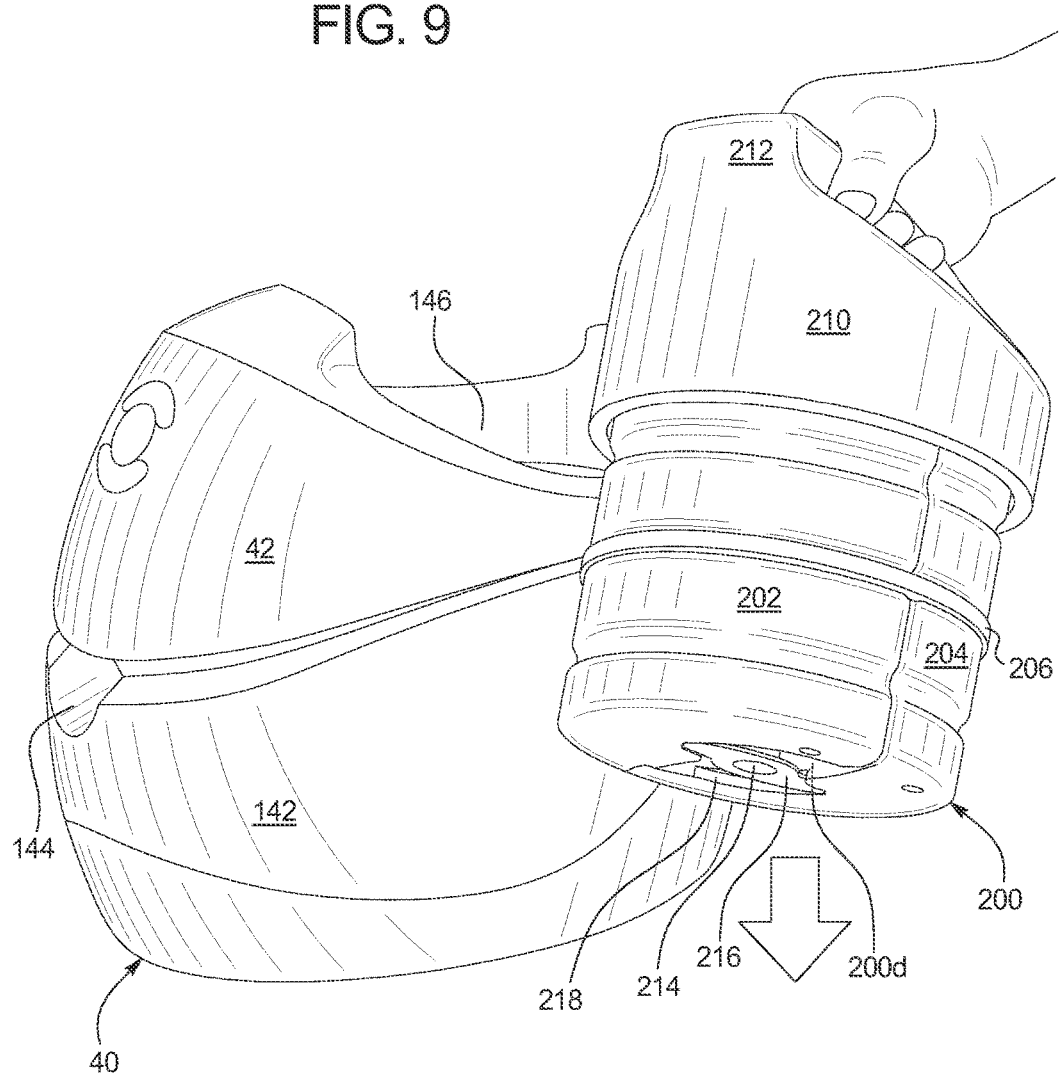

In FIG. 9, the patient removes assembly 200 from housing 42 and sets the assembly down as indicated by the arrow. Therapy water remains in housing 42, while containers 202 and 204 now likely contain only water or perhaps a small amount of ice. The therapy water remaining within housing 42 and containers 202 and 204 can be reused and does not need to be replaced. Thus the cumbersome prior art dumping of used water to make room for new ice is not necessary.

Figure 10:
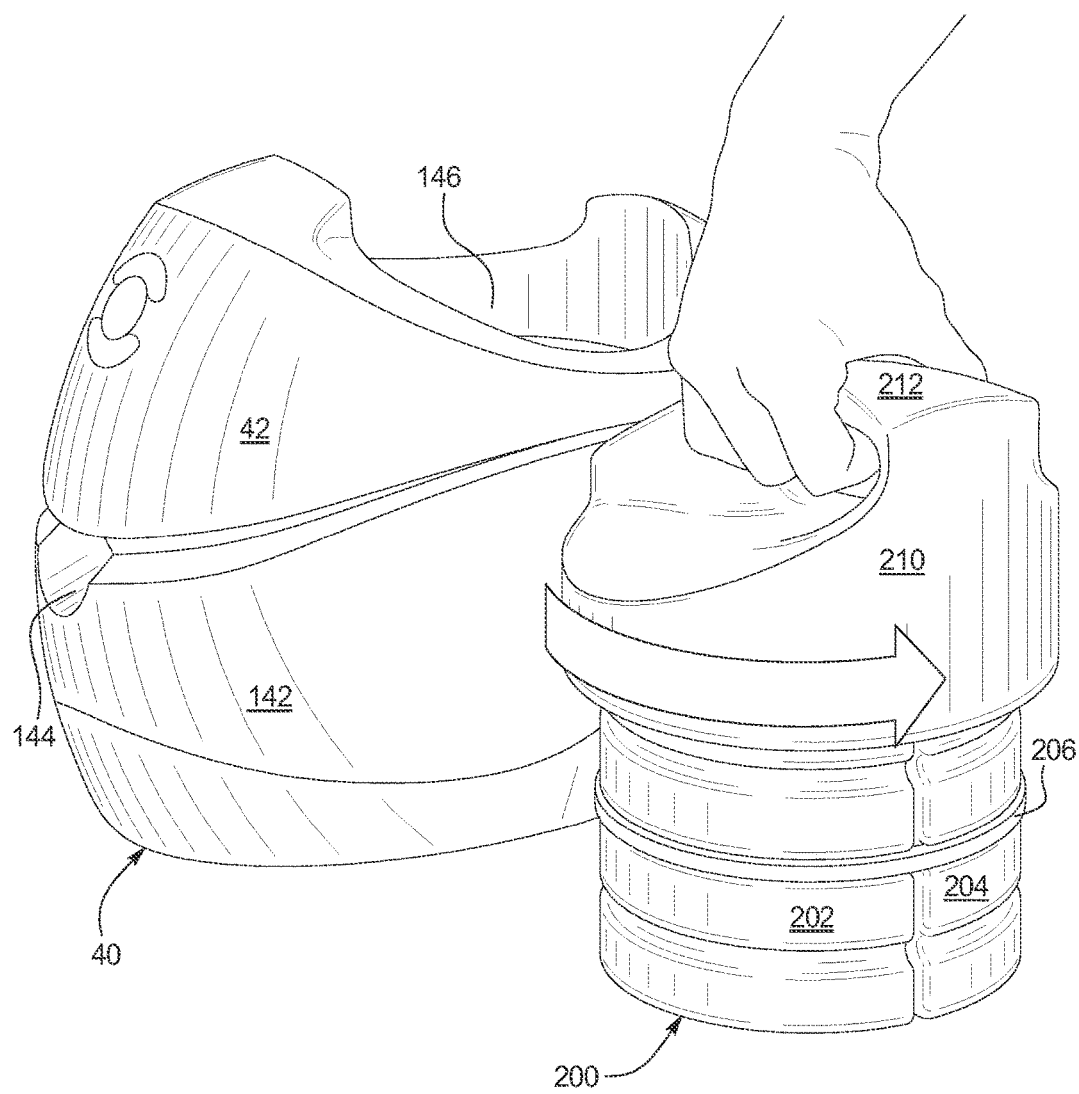

In FIG. 10, the patient rotates handle 212 counterclockwise as indicated by the arrow. This action causes flange 216 to rotate free from lower lips 218 of containers 202 and 204. Carrier 210 can then be lifted away and inserted onto the next or second set of frozen containers 202 and 204. The unfrozen containers 202 and 204 in FIG. 10 are placed in a freezer for refreezing.

Figure 11:
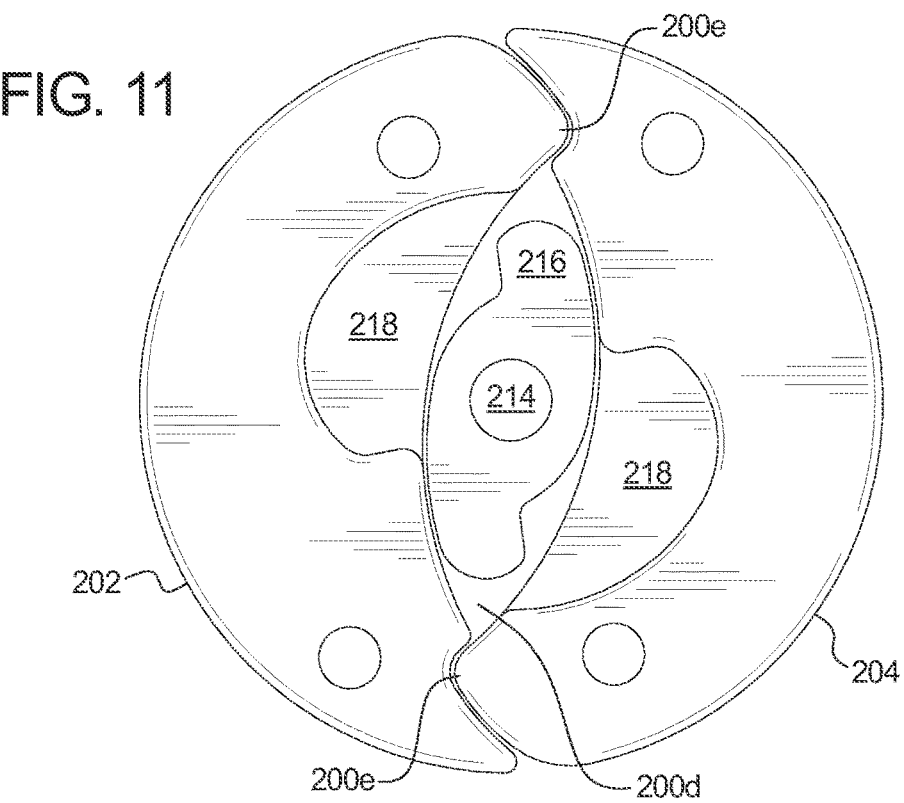
FIGS. 11 and 12 are bottom plan views of the ice container assembly of FIGS. 3 to 10 illustrating one embodiment for removably capturing the mated containers for transport.
Figure 12:
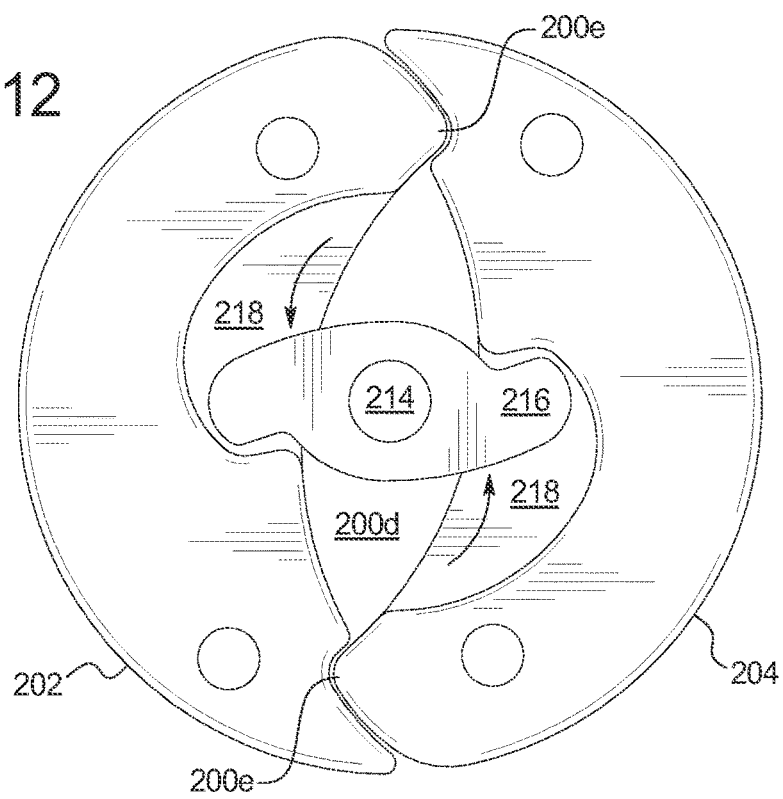

FIGS. 11 and 12 illustrate one embodiment for how carrier 210 locks to and comes free from containers 202 and 204 to respectively form and disassemble container assembly 200. In FIGS. 11 and 12, the distal end of stem 214 and flange 216 reside at the bottom of containers 202 and 204 as they do in FIGS. 5 to 9. To insert stem 214 into containers in 202 and 204 in FIG. 11, flange 216 needs to be turned to the position shown in FIG. 11, so that flange 216 can fit through the pointed oblong three-dimension space or volume 200d.

In FIG. 12, the user has turned handle 212 of carrier 210 clockwise from the top of assembly 200, which is seen as a counterclockwise turn from the bottom of assembly 200 as indicated by the arrows. Flange 216 turns likewise and slides beneath lips 218 of containers 202 and 204. The patient can now lift the entire assembly 200, wherein flange 216 catches lips 218 and holds containers 202 and 204 during lifting. To release carrier 210, the opposite action is performed, causing flange 216 to turn from the position of FIG. 12 to that of FIG. 11, after which carrier 210 can be pulled out of and free from containers 202 and 204.

Figure 13:
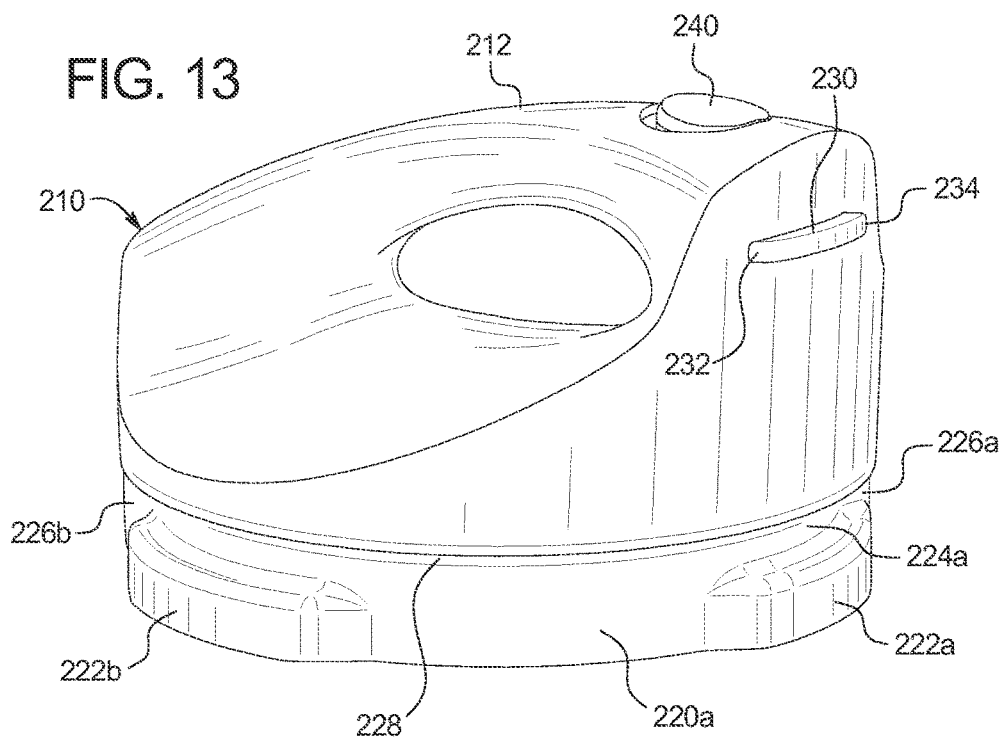
FIGS. 13 and 14 are side and top perspective views, respectively, illustrating one embodiment for reliably locking the ice container assembly into a cooling bath of the present disclosure.
Figure 14:
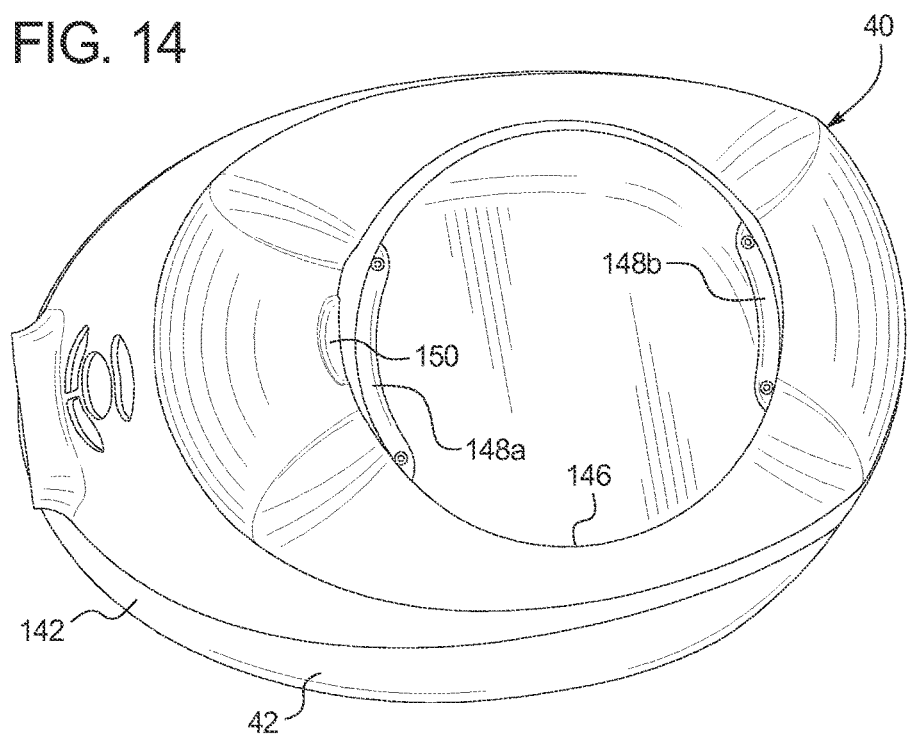

FIGS. 13 and 14 illustrate one embodiment for how assembly 200 locks to and comes free from cooling bath housing 42. As discussed above, when assembly 200 is locked to cooling bath housing 42, the user can use handle 212 of assembly 200 to transport the entire cooling bath 40. FIG. 13 illustrates carrier 210 and handle 212 in more detail. In the illustrated embodiment, carrier 210 includes a lower cylindrical portion having a series of breaks 220a (220b not viewable in FIG. 13) located between a series of circumferentially extending protrusions or ribs 222a and 222b. An annular passageway 224a extends from a stop 226a, along the top of rib 222a, along the top of break 220a, and along the top of rib 222b, to stop 226b. A similar annular passageway (224b, not viewable in FIG. 13) extends around the back of carrier 210, from stop 226b, along the top of a first non-viewable rib (222c), along the top of a non-viewable break (220b), and along the top of a second non-viewable rib (222d), to stop 226a.

FIG. 14 illustrates that bath housing 42 includes inwardly projecting, annularly extending beams 148a and 148b. Beams 148a and 148b are spaced apart one-hundred eighty degrees from each other as are breaks 220a and 220b of carrier 210. When carrier 210 is placed into large opening 146 of bath housing 42, and if carrier is properly offset such that handle 212 points towards about ten o'clock, while beam 148a resides at twelve o'clock, breaks 220a and 220b of carrier 210 enable the carrier to be set into housing 42 such that (i) ribs 222a to 222d fall below beams 148a and 148b, (ii) annular passageways 224a and 224b come into vertical alignment with beams 148a and 148b, and (iii) the top wall 228 of passageways 224a and 224b comes to rest on beams 148a and 148b. At this point, the user can turn handle 212 clockwise such that the handle moves to twelve o'clock as marked by beam 148a. Now, rib 222a resides beneath beam 148a and rib 222c (not viewable) resides beneath beam 148b. Stops 226a and 226b halt the clockwise rotation of carrier 210 at the rotational point where handle 212 is at twelve o'clock to complete the top of housing 42 as described above.

Carrier 210 includes a ramped projection 230 having a leading, non-raised ramp edge 232 followed by ramp that rises gradually from base edge 232 to a raised ramp edge 234. Ramped projection 230 is spring-loaded inside carrier 210 so as to be biased outwardly from a front surface of carrier 210. A button 240 is provided to enable the user to retract ramped projection 230 against the spring to enable carrier 210 to be lowered into opening 146. When carrier 210 is lowered into housing 42 and rotated from the about ten o'clock position to twelve o'clock, ramped projection 230 is rotated into communication with a mating notch 150 formed in housing 42 at the top and front of aperture 146. At twelve o'clock, ramped projection 230 is in full alignment with mating notch 150, such that the spring behind ramped projection 230 pushes the projection into the notch, removably locking carrier to housing 42. At this point the user can safely lift and move the entire cooling bath 40 via handle 212. When lifted, rib 222a catches beam 148a and rib 222c (not viewable) catches beam 148b, so that the entire bath is lifted. The locking of ramped projection 230 within mating notch 150 prevents housing 42 from rotating relative to carrier while handle 212 of carrier 210 is grasped by the user.

To remove a spent container assembly 200 from housing 42, the user retracts button 240 to likewise retract ramped projection 230. When button 240 is retracted, the patient can turn handle 212 and carrier 210 clockwise back to, for example, about ten o'clock relative to housing 42. At ten o'clock, the user can lift spent container assembly 200 from housing 42 for replacement. Carrier 210 comes free from containers 202 and 204 as has been described herein.

Figure 15:
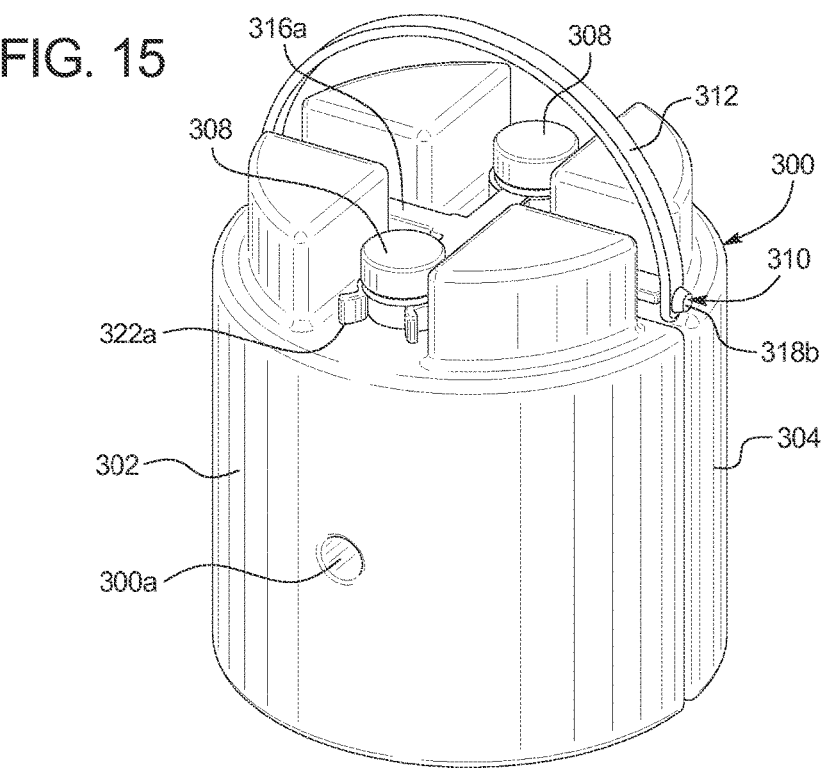
FIGS. 15 and 16 are perspective views of an alternative ice container assembly of the present disclosure.
Figure 16:
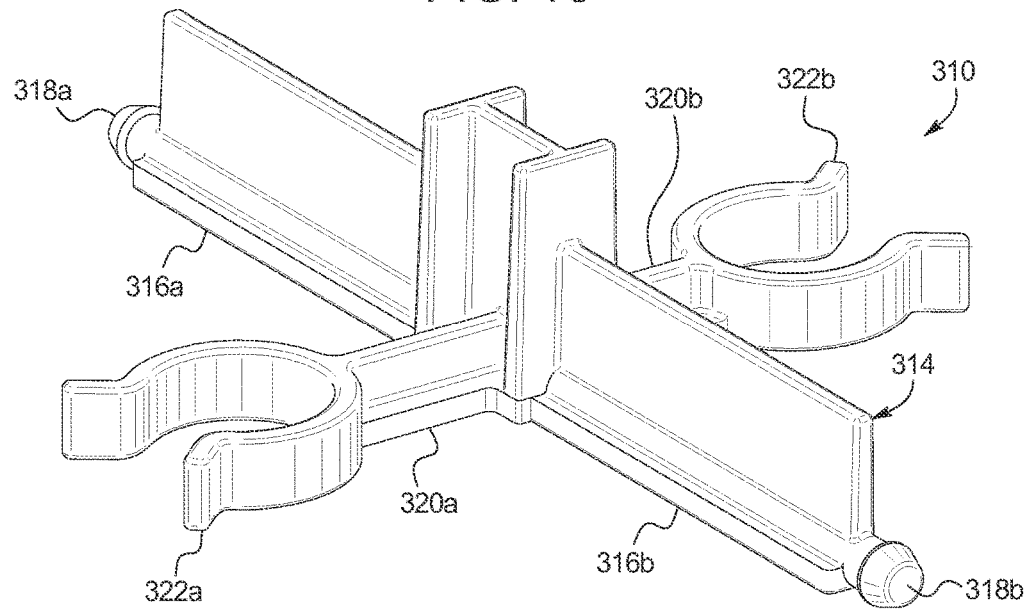

Referring now to FIGS. 15 and 16, an alternative ice container assembly 300 is illustrated. In FIG. 15, ice container assembly 300 includes bottles 302 and 304, which are held together via carrier 310 and moved by hinged handle 312 connected to carrier 310. Bottles 302 and 304 can be made of a suitable, e.g., plastic, material including any of the materials discussed above for bottles 202 and 204. Likewise, carrier 310 can be made of suitable, e.g., plastic, material including any of the materials discussed above for carrier 210. Bottles 302 and 304 again mate together to form a cylindrical ice-carrying tandem. Water flowpaths may be provided between containers 302 and 304, through holes, such as hole 300a, or around protrusions, indentations and/or irregularities formed along the sides of containers 302 and 304.

Bottles 302 and 304 can each include a removable cap 308 capping a necked container opening to accept water to make ice within container 302 and 304. Caps 308 at their lower edges are also sized to impinge against the tops of spring-clamps 322a and 322b of carrier 310, to help hold container assembly 300 together when the assembly is lifted for transport.

One suitable carrier for assembly 300 is carrier 310 illustrated in FIG. 16. Carrier 310 includes at least substantially orthogonally spaced apart legs 316a, 316b, 320a and 320b. Legs 316a and 316b terminate at snap-fitting hinge pins 318a and 318b, respectively. Legs 320a and 320b terminate at spring-clamps 322a and 322b, respectively. Legs 316a, 316b, 320a and 320b each include bends, gusseting and/or ribbing for stiffening. Any of the plastic components associated with cooling bath 40, assembly 200 or assembly 300 can be molded, e.g., injection molded.

As illustrated in FIG. 15, the distal ends of, e.g., semi-circular, handle 312 include apertures that snap-fit over hinge pins 318a and 318b. Handle 312 can thereafter rotate about hinge pins 318a and 318b relative to containers 302 and 304 and carrier 310. Spring-clamps 322a and 322b snap-fit around the cap-receiving neck portions of bottles 302 and 304. Again, the bottoms of caps 308 lock against the top edges of spring-clamps 322a and 322b when assembly 300 is lifted for transport. Spring-clamps 322a and 322b snap onto and off of bottles 302 and 304, respectively, to respectively hold the bottles during treatment and to swap out spent containers 302 and 304 during or after treatment with freshly frozen containers.

Additional Aspects of the Present Disclosure

Aspects of the subject matter described herein may be useful alone or in combination one or more other aspect described herein. Without limiting the foregoing description, in a first aspect of the present disclosure, a cold therapy system includes: a cooling bath; a therapy pad in fluid communication with the cooling bath; a pump positioned and arranged to pump water from the cooling bath to the therapy pad and back to the cooling bath; and a control unit controlling the pump, the control unit programmed to operate the pump according to a cycle in which the pump is operated at less than maximum to cause the therapy pad temperature to be raised and to conserve a cooling resource within the cooling bath.

In accordance with a second aspect of the present disclosure, which may be used in combination with any other aspect listed herein, the cycle is a flow-on/flow-off cycle.

In accordance with a third aspect of the present disclosure, which may be used in combination with any other aspect listed herein, the cycle is a high-flow/low-flow cycle.

In accordance with a fourth aspect of the present disclosure, which may be used in combination with any other aspect listed herein, the pump is operated at less than maximum for a particular percentage of time of the cycle.

In accordance with a fifth aspect of the present disclosure, which may be used in combination with any other aspect listed herein, the pump is positioned within the cooling bath.

In accordance with a sixth aspect of the present disclosure, which may be used in combination with any other aspect listed herein, the cooling resource is ice.

In accordance with a seventh aspect of the present disclosure, which may be used in combination with any other aspect listed herein, a cold therapy system includes: a cooling bath; a therapy pad in fluid communication with the cooling bath: a pump positioned and arranged to pump water from the cooling bath to the therapy pad and back to the cooling bath; a heat exchanger, a first pathway fluidly connecting the cooling bath to the heat exchanger, a second pathway fluidly connecting the heat exchanger to an inlet of the therapy pad: a third pathway fluidly connecting an outlet of the therapy pad to the heat exchanger; a fourth pathway fluidly connecting an outlet of the heat exchanger to the cooling bath; and a valve in the third or fourth pathway, the valve operated so as to cause the therapy pad temperature to be raised and to conserve a cooling resource within the cooling bath.

In accordance with an eighth aspect of the present disclosure, which may be used in combination with any other aspect listed herein including the seventh aspect, the system includes a control unit and wherein the valve is controlled via the control unit.

In accordance with a ninth aspect of the present disclosure, which may be used in combination with any other aspect listed herein including the seventh aspect, the valve is controlled mechanically or electromechanically.

In accordance with a tenth aspect of the present disclosure, which may be used in combination with any other aspect listed herein including the seventh aspect, the valve is controlled according to an opened/closed cycle.

In accordance with an eleventh aspect of the present disclosure, which may be used in combination with any other aspect listed herein, a cold therapy system includes: a cooling bath; a therapy pad in fluid communication with the cooling bath; a pump positioned and arranged to pump water from the cooling bath to the therapy pad and back to the cooling bath; and a heat exchanger including an insulating sleeve that surrounds (i) a first pathway carrying water from the cooling bath to the therapy pad and (ii) a second pathway carrying water from the therapy pad to the cooling bath, the heat exchanger further including at least one of (a) a conductive wall or separator between the first and second pathways, (b) a serpentine wall between the first and second pathways, (c) thin-walled first and second pathways, or (d) a metal foil surrounding the first and second pathways.

In accordance with a twelfth aspect of the present disclosure, which may be used in combination with any other aspect listed herein including the eleventh aspect, the heat exchanger further includes a spiral heat exchanging pathway.

In accordance with a thirteenth aspect of the present disclosure, which may be used in combination with any other aspect listed herein including the twelfth aspect, at least one of the pump or the spiral heat exchanging pathway is provided in the cooling bath.

In accordance with a fourteenth aspect of the present disclosure, which may be used in combination with any other aspect listed herein, a cold therapy system includes: a pump; a therapy pad in fluid communication with the pump; and a cooling bath in fluid communication with the pump, the cooling bath including a container in which ice has been premade and kept frozen, the cooling reservoir including space to hold the container and for liquid water to flow around the container.

In accordance with a fifteenth aspect of the present disclosure, which may be used with any other aspect listed herein including the fourteenth aspect, including the fourteenth aspect, the pump is submerged in the cooling bath.

In accordance with a sixteenth aspect of the present disclosure, which may be used with any other aspect listed herein including the fourteenth aspect, the container is removably mounted to a carrier for placement inside the cooling bath.

In accordance with a seventeenth aspect of the present disclosure, which may be used with any other aspect listed herein including the fourteenth aspect, the system includes a plurality of containers, wherein a first one of the containers is placed in the cooling bath for use, while a second one of the containers is kept frozen for replacement use.

In accordance with an eighteenth aspect of the present disclosure, which may be used with any other aspect listed herein including the fourteenth aspect, the system includes a plurality of ice-holding containers removably interlocked together.

In accordance with a nineteenth aspect of the present disclosure, which may be used any other aspect listed herein including the eighteenth aspect, the ice-holding containers are interlocked such that water can flow between the containers.

In accordance with a twentieth aspect of the present disclosure, which may be used with any other aspect listed herein including the eighteenth aspect, the interlocked containers are further configured to be removably mounted to a carrier for transport.

In accordance with a twenty-first aspect of the present disclosure, which may be used with any other aspect listed herein including the twentieth aspect, the carrier and the interlocked containers are structured and arranged such that the carrier rotates onto and off of the interlocked containers.

In accordance with a twenty-second aspect of the present disclosure, which may be used with any other aspect listed herein including the eighteenth aspect, the cooling bath includes space to hold the plurality of interlocked containers and liquid water to flow around the containers.

In accordance with a twenty-third aspect of the present disclosure, which may be used with any other aspect listed herein, a cold therapy method includes: configuring a container to store liquid water; forming the container of a material that can withstand the liquid water being frozen into ice; sizing the container such that the container can be stored in a freezer to freeze the liquid water; sizing the container and a cooling bath such that liquid water can be pumped within the bath and around the container to cool the pumped liquid water, and enabling the container to be removed from the cooling bath after a period of use such that a frozen replacement container can be placed into the cooling bath without having to remove any pumped liquid water.

In accordance with a twenty-fourth aspect of the present disclosure, which may be used with any other aspect listed herein including the twenty-third aspect, the method includes enabling a plurality of containers to be removably coupled together for placement into the removal from the cooling bath.

In accordance with a twenty-fifth aspect of the present disclosure, which may be used with any other aspect listed herein including the twenty-fourth aspect, wherein removably coupling the containers together includes releasably locking the containers to a carrier for carrying the containers.

In accordance with a twenty-sixth aspect of the present disclosure, which may be used with any other aspect listed herein including the twenty-fifth aspect, the method includes enabling the carrier to releasably lock to the cooling bath for carrying the bath and the containers.

In accordance with a twenty-seventh aspect of the present disclosure, any of the structure and functionality illustrated and described in connection with FIGS. 1 to 16 may be used in combination with any aspect listed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A cold therapy system comprising:
   a cooling bath including a cavity therein configured to hold a cooling resource and liquid water;
   a therapy pad in fluid communication with the cavity of the cooling bath;
   a pump positioned and arranged to pump liquid water from the cavity of the cooling bath to the therapy pad and to pump liquid water from the therapy pad back to the cavity of the cooling bath;
   a heat exchanger external to liquid water held within the cavity of the cooling bath, wherein the heat exchanger is in fluid communication with the cavity of the cooling bath and the therapy pad and is positioned and arranged to exchange heat between liquid water flowing from the cavity of the cooling bath to the therapy pad and liquid water flowing from the therapy pad back to the cavity of the cooling bath; and
   a control unit configured to control the pump, the control unit programmed to operate the pump according to at least one of: (i) a flow-on/flow-off cycle during treatment or (ii) a high-flow/low-flow cycle during treatment, to adjust the therapy pad temperature and/or to conserve the cooling resource held within the cavity of the cooling bath.

2. The cold therapy system of claim 1, wherein the flow-on/flow-off cycle is electronically and automatically controlled by the control unit.

3. The cold therapy system of claim 1, wherein the control unit is further programmed to control the pump to switch between the flow-on/flow-off cycle and the high-flow/low-flow cycle.

4. The cold therapy system of claim 1, wherein the pump is operated at less than maximum for a particular percentage of time during the flow-on/flow-off cycle.

5. The cold therapy system of claim 1, wherein the pump is positioned to be submerged under liquid water within the cavity of the cooling bath.

6. The cold therapy system of claim 1, wherein the cooling resource is ice.

7. The cold therapy system of claim 1, wherein the cooling resource is ice;
   the system further comprising a fluid-tight container for holding the ice, the container positioned within the cavity of the cooling bath so that liquid water within the cavity of the cooling bath contacts the container, but not the ice held in the container.

8. The cold therapy system of claim 7, wherein the pump is submerged in liquid water within the cavity of the cooling bath.

9. The cold therapy system of claim 7, wherein the container is removeably mounted to a carrier for positioning the container within the cavity of the cooling bath.

10. The cold therapy system of claim 7, wherein the container is a first container, the cold therapy system further comprising a second fluid-tight container for holding ice, wherein the first container is placed in the cavity of the cooling bath for use, while the second container is configured to be kept frozen for replacement use.

11. The cold therapy system of claim 7, wherein the container is a first container, the cold therapy system further comprising a second fluid-tight container for holding ice, wherein the first and second containers are removeably interlocked together.

12. The cold therapy system of claim 11, wherein the ice-holding first and second containers are interlocked such that water can flow between the first and second containers.

13. The cold therapy system of claim 11, wherein the interlocked first and second containers are further configured to be removeably mounted to a carrier for transport.

14. The cold therapy system of claim 13, wherein the carrier and the interlocked first and second containers are structured and arranged such that the carrier rotates onto and off of the interlocked first and second containers.

15. The cold therapy system of claim 11, wherein the interlocked first and second containers are positioned within the cavity of the cooling bath so that liquid water flows around the first and second containers.

16. The cold therapy system of claim 1, wherein the heat exchanger is positioned and arranged to avoid contact between liquid water flowing from the cavity of the cooling bath to the therapy pad and liquid water flowing from the therapy pad back to the cavity of the cooling bath within the heat exchanger.

17. The cold therapy system of claim 1, wherein the control unit is programmed to operate the pump according to the high-flow/low-flow cycle during treatment.

18. A cold therapy system comprising:
   a cooling bath configured to hold a cooling resource and liquid water;
   a therapy pad in fluid communication with the cooling bath;
   a pump positioned and arranged to pump liquid water from the cooling bath to the therapy pad and to pump liquid water from the therapy pad back to the cooling bath;
   a heat exchanger having a chilled water inlet, a chilled water outlet, a heated water inlet and a heated water outlet;
   a first pathway fluidly connecting the cooling bath to the chilled water inlet of the heat exchanger;
   a second pathway fluidly connecting the chilled water outlet of the heat exchanger to the therapy pad;
   a third pathway fluidly connecting the therapy pad to the heated water inlet of the heat exchanger;
   a fourth pathway fluidly connecting the heated water outlet of the heat exchanger to the cooling bath;
   a bypass branch fluidly connecting the therapy pad and the cooling bath while bypassing the heat exchanger;
   a valve positioned downstream of the therapy pad enabling at least some liquid water from the therapy pad to bypass the heat exchanger via the bypass branch and flow to the cooling bath without flowing through the heat exchanger; and
   a control unit in electrical communication with the valve and configured to automatically control the valve based on a sensed temperature so as to adjust the therapy pad temperature and/or to conserve the cooling resource held within the cooling bath,
   wherein liquid water circulates through the first, second, third and fourth pathways by flowing from the cooling bath to the chilled water inlet of the heat exchanger via the first pathway, from the chilled water outlet of heat exchanger to the therapy pad via the second pathway, from the therapy pad to the heated water inlet of the heat exchanger via the third pathway, and from the heated water outlet of the heat exchanger to the cooling bath via the fourth pathway and/or circulates through the first and second pathways and the bypass branch by flowing from the cooling bath to the chilled water inlet of the heat exchanger via the first pathway, from the chilled water outlet of heat exchanger to the therapy pad via the second pathway, and from the therapy pad to the cooling bath via the bypass branch.

19. The cold therapy system of claim 18, wherein the valve is controlled according to a high-flow/low-flow cycle.

20. The cold therapy system of claim 18, wherein liquid water flowing from the cooling bath to the therapy pad through the heat exchanger via the chilled water inlet and the chilled water outlet of the heat exchanger and liquid water flowing from the therapy pad to the cooling bath through the heat exchanger via the heated water inlet and the heated water outlet of the heat exchanger are in fluid isolation from one another within the heat exchanger.

21. The cold therapy system of claim 18, wherein the valve is controlled according to an opened/closed cycle.

22. The cold therapy system of claim 18, wherein the therapy pad has a pad inlet, a pad outlet and a patient cooling pathway extending between the pad inlet and the pad outlet and liquid water circulates through the therapy pad from the pad inlet to the pad outlet via the patient cooling pad pathway, further wherein the cold therapy system is configured so that the volume of liquid water discharged from the pad outlet over a treatment time period is equal to the volume of liquid water discharged into the cooling bath from the bypass branch and the fourth pathway over the same treatment time period.

23. A cold therapy system comprising:
a cooling bath configured to hold liquid water;
a therapy pad in fluid communication with the cooling bath;
a pump positioned and arranged to pump liquid water from the cooling bath to the therapy pad and to pump liquid water from the therapy pad back to the cooling bath;
a heat exchanger external to liquid water held within the cooling bath, wherein the heat exchanger includes a first spiral chamber carrying water from the cooling bath to the therapy pad and a second spiral chamber carrying water from the therapy pad to the cooling bath or includes first and second lumens disposed parallel to each other, (i) the first lumen carrying water from the cooling bath to the therapy pad and (ii) the second lumen carrying water from the therapy pad to the cooling bath, wherein only a thin heat-conductive wall separates the first lumen from the second lumen and/or a bendable metal longitudinally abuts the first lumen and the second lumen.

24. The cold therapy system of claim 23, wherein the cooling bath includes a housing and a cavity within the housing configured to hold liquid water and the heat exchanger is mounted to the housing of the cooling bath.

25. The cold therapy system of claim 23, wherein the heat exchanger includes the first and second lumens.

26. The cold therapy system of claim 25, wherein the first lumen is separated from the second lumen by only the thin heat-conductive wall.

* * * * *